(12) United States Patent
Yamaya et al.

(10) Patent No.: US 8,594,404 B2
(45) Date of Patent: Nov. 26, 2013

(54) PET SCANNER AND IMAGE RECONSTRUCTION METHOD THEREOF

(75) Inventors: Taiga Yamaya, Chiba (JP); Hideo Murayama, Chiba (JP); Shinichi Minohara, Chiba (JP)

(73) Assignee: National Institute of Radiological Sciences, Chiba-Shi (JP)

( * ) Notice: Subject to any disclaimer, the term of this patent is extended or adjusted under 35 U.S.C. 154(b) by 969 days.

(21) Appl. No.: 12/450,803

(22) PCT Filed: Apr. 17, 2007

(86) PCT No.: PCT/JP2007/058361
§ 371 (c)(1),
(2), (4) Date: Oct. 14, 2009

(87) PCT Pub. No.: WO2008/129666
PCT Pub. Date: Oct. 30, 2008

(65) Prior Publication Data
US 2010/0128956 A1 May 27, 2010

(51) Int. Cl.
*A61B 6/03* (2006.01)
(52) U.S. Cl.
CPC ........................................ *A61B 6/03* (2013.01)
USPC ................. 382/131; 250/363.02; 250/363.03; 250/363.04; 250/363.05
(58) Field of Classification Search
CPC ....................................................... A61B 6/03
USPC .......................... 250/363.02–363.05; 382/131
See application file for complete search history.

(56) References Cited

U.S. PATENT DOCUMENTS

| | | | |
|---|---|---|---|
| 6,490,476 B1 | 12/2002 | Townsend et al. | |
| 6,831,961 B1 * | 12/2004 | Tybinkowski et al. | 378/4 |
| 2003/0012331 A1 | 1/2003 | Kojima et al. | |
| 2003/0118155 A1 * | 6/2003 | Ueno et al. | 378/177 |
| 2003/0179853 A1 * | 9/2003 | Amemiya et al. | 378/63 |
| 2004/0097800 A1 * | 5/2004 | Crosetto | 600/407 |
| 2005/0109943 A1 * | 5/2005 | Vaquero et al. | 250/363.04 |
| 2007/0080295 A1 * | 4/2007 | Hamill | 250/363.03 |

FOREIGN PATENT DOCUMENTS

| | | | | |
|---|---|---|---|---|
| JP | 01027569 A | * | 1/1989 | |
| JP | 04268484 A | * | 9/1992 | |
| JP | A 5-150046 | | 6/1993 | |
| JP | 09033658 A | * | 2/1997 | |
| JP | A 9-211130 | | 8/1997 | |
| JP | A 2001-141827 | | 5/2001 | |

(Continued)

OTHER PUBLICATIONS

PTO 13-4138 which is an nglish translation of Yamamoto et al. (JP04268484A).*

(Continued)

*Primary Examiner* — Minh-Toan Ton
*Assistant Examiner* — John Corbett
(74) *Attorney, Agent, or Firm* — Oliff & Berridge, PLC

(57) ABSTRACT

A plurality of detector rings in which detectors arranged densely or spatially in a ring shape or in a polygonal shape are arranged, with an open space kept in the body axis direction, coincidences are measured for some of or all of detector pairs connecting the detector rings apart from the open space to perform three-dimensional image reconstruction, thereby imaging the open space between the detector rings as a tomographic image. Therefore, the open space is secured, with the deteriorated quality of an image suppressed, thus making it possible to easily gain access to a patient under PET scanning from outside a gantry and also provide irradiation of particle beams for cancer treatment as well as X-ray CT scanning.

8 Claims, 32 Drawing Sheets

(56) References Cited

FOREIGN PATENT DOCUMENTS

| | | |
|---|---|---|
| JP | A 2003-79614 | 3/2003 |
| JP | A 2004-181204 | 7/2004 |

OTHER PUBLICATIONS

Iida et al., "A New PET Camera for Noninvasive Quantitation of Physiological Functional Parametric Imagas: Headtome-V-Dual," *Quantification of BrainFunction Using PET*, Chapter 12, pp. 57-61, Academic Press, 1996.

Crespo et al., "On the detector arrangement for in-beam PET for hadron therapy monitoring," *Phys. Med. Biol.*, vol. 51, 2006, pp. 2143-2163.

Jul. 6, 2010 Office Action issued in Japanese Patent Application No. 2009-510700 (with translation).

\* cited by examiner (A)

(B)

(A)

(B)

(A)

(B)

PET SCANNER AND IMAGE RECONSTRUCTION METHOD THEREOF

TECHNICAL FIELD

The present invention relates to positron emission tomography equipment (also called a positron CT scanner and hereinafter referred to as a PET scanner) in which a radiopharmaceutical labeled with a positron emission nuclide is injected into the body, each pair of annihilation (gamma) photons resulting from decay of positrons is determined according to the principle of coincidence, and image reconstruction is performed to image the spatial and temporal distribution of the radiopharmaceutical. The present invention relates, in particular, to an open-type PET scanner capable of securing open spaces inside the scanner and also to an image reconstruction method thereof.

BACKGROUND ART

PET (Positron Emission Tomography) is a method for injecting radiopharmaceuticals labeled with a positron emission nuclide into the body to image the spatial and temporal distribution of the radiopharmaceuticals. In particular, PET scanning in which a radiopharmaceutical called fludeoxyglucose (FDG) is used has become the focus of attention because of the usefulness in making an early diagnosis of cancers over the entire body.

In PET, a radiopharmaceutical to be injected is selected to obtain information on various functions of the brain and organs. It was, however, difficult to accurately localize a site of cancer, if the cancer was found, due to the shortage of anatomical information. It is described that X-ray CT images are structural images, while PET images are functional images. In response to the above-described demands, PET/CT scanners capable of performing PET and X-ray CT scanning continuously on the same bed have been made commercially available from many companies, thus greatly contributing to the widespread use of FDG-PET.

On the other hand, it is also important to treat cancers found by a PET diagnosis or others. A method for treating cancers by using nuclear radiation, unlike conventional surgical procedures or chemotherapies has become the focus of attention. In particular, particle radiotherapy in which heavy ion particle beams or proton beams are irradiated only at a cancer site has gained a great deal of attention as a method for providing excellent therapeutic effects and characteristics of acutely concentrated irradiation to lesions. Irradiation is performed by controlling accurately the direction and dosage of beams according to treatment plans carefully calculated on the basis of X-ray CT images which have been taken separately. However, in reality, it is difficult to confirm accurately whether irradiation has been performed in accordance with treatment plans or not. If the patient is positioned wrongly to result in deviation of the irradiation field, the deviation is not easily detected. Therefore, a method in which PET is used to monitor the irradiation field of particle beams in real time is now gaining attention. According to this method, a PET radiopharmaceutical is not injected but annihilation radiation resulting from projectile fragmentation reactions or target nuclear spallation reactions by beam irradiation is imaged by using the principle of PET. Since a site at which the annihilation radiation is generated is strongly correlated with the dosage distribution of irradiation beams, this method is expected to monitor treatment.

The principle of PET is as follows. As shown in FIG. 1, positrons emitted from a positron emission nuclide 8 by the decay of positrons undergo pair annihilation with electrons in the vicinity, and the thus generated pair of annihilation (gamma) photons $8a$, $8b$ at 511 keV are determined by a pair of radiation detectors $10a$, $10b$ according to the principle of coincidence. Thereby, the position at which the nuclide 8 is present can be localized on one line segment connecting between the pair of detectors $10a$, $10b$ (coincidence line: line-of-response: LOR). When an axis from the head of a patient to the feet is defined as a body axis, a distribution of the nuclide on a planar surface intersecting perpendicularly with the body axis is obtained by image reconstruction in two-dimensional mode from data of the coincidence line determined on the planar surface in various directions.

Therefore, as shown in FIG. 2 (A) covering a polygonal-type PET scanner and in FIG. 2 (B) covering a ring-type PET scanner, earlier PET scanners were provided with a constitution to arrange detectors 10 on a planar surface which was given as a field-of-view (FOV) in such a manner as to surround the FOV in a polygonal shape (A) or a ring shape (B). In FIG. 2 (B), numeral 6 depicts a patient and that of 11 depicts a detector ring.

In the 1990s, as illustrated in FIG. 3 (A) covering a multi-layer polygonal-type PET scanner and in FIG. 3 (B) covering a multi-layer ring-type PET scanner, 3-D mode PET scanners were developed one after another in which detector rings 11 were arranged in the body axis direction of the patient 6 to give a multiple ring 12, thereby a FOV in two-dimensional mode was changed to that in three-dimensional mode, and the coincidence was also determined between the detector rings 11 to increase the sensitivity greatly.

On the other hand, as illustrated in FIG. 4, gamma camera opposition-type PET scanners which rotate gamma cameras 14 arranged in opposition have also been developed. However, this type of PET scanner is insufficient in sensitivity due to the limited solid angle of a detector, with no widespread use. Positron imaging equipment in which cameras are not rotated has been commercially available mainly for experimental uses. The equipment is to obtain planar images parallel with the face of the detector and not for tomography (corresponding not to X-ray CT but to radiography in X-ray equipment).

In order to increase the resolution of an image in view of the principle of image reconstruction, it is necessary that coincidence lines are obtained densely.

The detector sensitivity of a PET scanner is important in increasing the accuracy of an image. The detector sensitivity is generally considered insufficient. In order to compensate for the insufficiency, the dosage of a injecting nuclide at about 5 mCi (=185 MBq) (an effective dosage equivalent to about 40 times higher than that used in X-ray photograph of the chest) and the scanning time which is long, about 30 minutes are required. These factors cause mental and physical burdens to patients and are also one of the reasons that medical institutions cannot lower examination costs.

Therefore, in order to increase the detection sensitivity, recently developed PET scanners tend to array detectors, with no clearance left therebetween, and also arrange them long in the body axis direction. A patient port 13 (refer to FIG. 3) is approximately about 60 cm in diameter and from 40 cm up to 100 cm long in the body axis direction.

However, there is such a problem that a long patient port further increases the closed nature of the port, thereby causing psychological stress to patients. In particular, a PET scanner is frequently used not only in cancer screening tests for healthy people but also in examinations for patients having various types of diseases including mental disorders. Therefore, it is strongly desired to reduce the psychological stress to patients. A situation in which a patient under PET scanning is not visually confirmed for health conditions is not desirable also for medical personnel who perform PET scanning. Further, in research for understanding brain functions, many experiments are conducted in which blood samples are taken at intervals of several minutes during PET scanning or visual stimulations are given to visualize reactions inside the brain by using PET. The long patient port causes problems in these experiments as well.

Further, where a PET scanner is used to monitor particle radiotherapy in real time, not only a site to be treated can be determined during the same session by the PET scanner but also a PET scanner is required to be high in sensitivity because annihilation radiation resulting from irradiation is at a trace amount as compared with the amount of nuclide injected on ordinary PET scanning. In order to realize the high sensitivity, detectors must be arranged densely and extensively. However, since the detectors are not to block particle beams, it was difficult to arrange the detectors on the PET scanner in such a manner as to meet simultaneously the above-described two conditions. In the Gesellschaft für Schwerionenforschung mbH (GSI) of Germany and the National Cancer Center (Hospital East) of Japan, the rotational opposition-type PET scanner shown in FIG. 5 (A) is used to monitor treatment. Gamma camera opposition-type PET scanners can be easily arranged so as not to block particle beams 22 irradiated from a therapeutic radiation controller 20 but definitely hold a disadvantage in that the detector sensitivity is fundamentally lower.

A research group in Germany has proposed a fixed slit-type PET scanner as shown in FIG. 5(B) in which a slit 12s is made on the side of a multilayer ring PET scanner for allowing beams to pass through, making evaluation based on the computer simulation. However, the slit lacks necessary information for image reconstruction because of the presence of the slit, resulting in the deteriorated quality of an image, which is regarded as a problem (P. Crespo, et al., "On the detector arrangement for in-beam PET for hadron therapy monitoring," Phys. Med. Biol. Journal, vol. 51 (2006) pp. 2143-2163).

FIG. 6 illustrates a representative constitution of a conventional PET/CT scanner (refer to U.S. Pat. No. 6,490,476 B1). In this drawing, the numeral 32 depicts an X-ray tube of the X-ray CT scanner 30, and the numeral 34 depicts an X-ray detector, both of which are rotated to perform scanning. There is now available a type in which each of the PET scanner and the X-ray CT scanner is provided with a completely independent gantry and a type in which they are housed into one gantry in an integrated manner. The PET scanner and the X-ray CT scanner may be arranged in a different order, depending on the type, but they are always arranged in tandem inside the gantry. In terms of the movement of a bed 7, there is a type in which a gantry moves with respect to a fixed bed and a type in which a bed moves with respect to a fixed gantry.

Whichever the type may be, in a conventional PET/CT scanner, a field of view (FOV) of the PET is not in agreement with that of X-ray CT, or is several dozen centimeters apart from each other. There is found a potential problem that the same site is not determined during the same session by PET and X-ray CT. In the conventional PET/CT scanner, a bed is moved relatively with respect to a gantry, that is, a temporal difference is given, by which the same site can be imaged by PET and X-ray CT. In currently available FDG-PET check-ups, scanning is performed in several minutes at each site due to the fact that a radiopharmaceutical moves slowly in the body and the sensitivity is lower. For this reason, the above-described temporal difference is not recognized as a problem. However, a discrepancy between PET images and X-ray CT images on the chest which entails the deformation by respiration is found. This discrepancy is now recognized as a serious problem.

Thanks to the recently advanced development of PET scanners and PET radiopharmaceuticals, new PET radiopharmaceuticals and PET scanners extremely high in sensitivity will become available. Therefore, increased demand can be expected for imaging the pharmacokinetics inside the body at a higher speed. In this instance, the above-described temporal difference may be recognized as a problem.

A FOV of the conventional PET scanner in the body axis direction is limited to about 20 cm. Therefore, a bed is moved over several dozen minutes intermittently or continuously to image an entire body of a patient. Therefore, a site apart at a greater distance than the FOV in the body axis direction cannot be imaged theoretically during the same session. Although there are problems such as complicated data processing, the greatest reason for the limited FOV in the body axis direction is the increased equipment cost due to a greater number of detectors. On the other hand, there is a strong demand for expansion of the FOV in the body axis direction. For example, the Research Institute for Brain and Blood Vessels Akita conducted research in which two commercially available PET scanners were arranged together to image brain and heart regions during the same session and independently from each other (H. Iida, et al., "A New PET Camera for noninvasive quantitation of physiological functional parametric images. HEADTOME-V-Dual.," Quantification of brain function using PET (eds. R. Myers, V. Cunningham, D. Bailey, T. Jones) p. 57-61, Academic Press, London, 1996).

In the above constitution, although the FOV in the body axis direction is expanded intermittently, an increasing number of detectors are installed to raise the cost. Further, since each of the PET scanners makes an independent coincidence determination, no detection can be made for the radiation from a nuclide present at a region between the scanners, thus resulting in a failure in imaging the region between the scanners.

In positron imaging equipment not for tomography but for planar imaging, an idea has been proposed that detectors are arranged at sparsely spaced clearances, thereby sampling of the coincidence line can be sparsely performed to increase the uniformity and also expand a FOV (Japanese Published Unexamined Patent Application No. Hei 9-211130 and Japanese Published Unexamined Patent Application No. 2001-141827).

However, where this idea is applied as it is to a PET scanner so that detectors are arranged sparsely on a ring, the coincidence line necessary for image reconstruction is lacking to inevitably result in the deteriorated quality of an image.

On the other hand, Japanese Published Unexamined Patent Application No. Hei 5-150046 has proposed a method in which a FOV different from that which is imaged by a PET scanner as a tomographic image is measured simply at low cost as a projected image. As illustrated in FIG. 7, this method assumes such a case that the head of a subject 101 is measured by using a PET scanner (detector 102) and the heart is measured during the same session for the conditions by using another device (detector 105). This method may have demand for an activation test or the like in which, for example, $^{15}$O-labeled water is injected to measure the change in local cerebral blood flow in response to stimulation. Images of the brain must be obtained as tomographic images. Regarding the heart, only monitoring of blood flow pumped by the heart will be sufficient. Therefore, this method is considered to assume that a PET scanner for obtaining tomographic images and positron imaging equipment for obtaining projected images are arranged in tandem. Specifically, the PET scanner needs the image reconstruction for obtaining tomographic images, while the positron imaging equipment does not need the image reconstruction because measured data in itself is a projected image. In this method, some of the detectors used in the PET scanner also act as detectors of the positron imaging equipment, thereby providing an advantage that these two sets of equipment are combined into one set of integrated equipment to reduce the cost. In FIG. 7, the numerals 103 and 106 depict coincidence circuits, and those of 104 and 107 depict data processors.

The above method is to expand a FOV, however, it may be considered to secure an open space from a different point of view. However, provided by the detector 5 is not a tomographic image but a projected image.

Japanese Published Unexamined Patent Application No. Hei 5-150046 has also proposed that a plurality of detectors 5 are arranged to pick up projected images at the same time in various directions but has not described a point where an image is reconstructed to obtain a tomographic image.

DISCLOSURE OF THE INVENTION

The present invention has been made in order to solve the above-described conventional problems, and an object of which is to provide a PET scanner capable of suppressing the deteriorated quality of an image and also securing an open space for easily gaining access to a patient and fixing a medical device as well as to provide a method for the image reconstruction thereof.

Ordinarily, a PET scanner is structured so as to have a multiple ring detector in which detector rings are arranged in the body axis direction. There is a two-dimensional mode collection in which only coincidence lines (LORs) between the same rings are determined, as illustrated in FIG. 8 (A), and a three-dimensional mode collection in which all LORs including those between different rings are determined, as shown in FIG. 8 (B). On the other hand, the volume of tomographic images is that in which two dimensional slices are arranged in the body axis direction. Therefore, the volume of three-dimensional images can be theoretically reconstructed only from the two-dimensional mode collection data. Specifically, although the three-dimensional mode collection data is redundant, in reality, the count number is limited, and all LORs are therefore subjected to the three-dimensional image reconstruction for a reduction in noises.

In the present invention, with attention given to the data redundancy of PET image reconstruction in the three-dimensional mode, some of the detector rings are removed to secure a physically separated open space and also information lacking is compensated by LORs between remaining detector rings to perform image reconstruction, thus making it possible to image an open space. FIG. 9 illustrates an example of LORs in which a $4^{th}$ detector ring and a $5^{th}$ detector ring are removed from a PET scanner made up of eight detector rings. Annihilation radiation resulting from the nuclide in the open space can be determined by LORs between rings in the back and forth direction.

The present invention has been made, with attention given to the above description, more specifically, a plurality of detector rings in which detectors arranged densely or spatially in a ring shape or in a polygonal shape are arranged, with an open space kept in the body axis direction, coincidences are measured for some of or all of detector pairs connecting the detector rings apart from the open space to perform three-dimensional image reconstruction, thus imaging the open space between the detector rings as a tomographic image, by which the above-described problem is solved.

At this time, the coincidences may be measured not only for some of or all of detector pairs connecting detector rings apart from the open space but also for some of or all of detector pairs within the same detector rings to perform the three-dimensional image reconstruction, thus making it possible to image as a tomographic image a continuous region which combines a FOV within each of the detector rings with the open space.

Further, among open spaces secured between the detector rings, the detectors may be arranged at unnecessary open spaces, thus making it possible to improve the detector sensitivity and also improve the quality of a PET image.

Further, a gantry in itself may be completely or partially separated at the above-described open space, by which it is possible to gain access to a patient from outside the gantry.

Further, each of the thus separated detector rings may be structured so as to tilt in the back and forth direction as well as in the lateral direction or so as to move in the back and forth direction, or structured in such a manner that combines the above two cases, and a clearance between the detector rings in the body axis direction is made variable.

Still further, a medical device may be inserted at least partially into an open space between the detector rings, thus making it possible to monitor treatment, by which a site to be treated can be confirmed by a PET scanner during the same session with the treatment.

In addition, an X-ray CT scanner may be installed at least partially at a clearance region between detector rings, thus making it possible to image the same site during the same session with the X-ray CT scanner.

The present invention is to provide an image reconstruction method for PET scanners in which on calculating the image reconstruction of any of the PET scanners described so far, a system matrix to be calculated or referred is changed in accordance with the arrangement of detectors.

Since the PET scanner of the present invention is provided with an open space secured in separation from a patient port, it is possible not only to provide PET scanning for a patient with mental disorders but also to reduce psychological stress to a patient under examination which has proved to be an obstacle also in cancer screening for healthy people. Thereby, care can easily be given for patients under examination.

Further, medical devices for radiation or particle beams may be arranged at an open space in a combined manner, thus making it possible to secure a route of therapeutic beams to a patient, with the sensitivity of the PET scanner kept. For this reason, it is possible to easily monitor cancer treatment in real time by using heavy particle beams or proton beams.

Still further, an X-ray CT scanner may be arranged at an open space in a combined manner, by which the FOV of the X-ray CT scanner can be set in the FOV of a PET scanner to realize a PET/CT scanner capable of imaging the same site during the same session.

BEST MODE FOR CARRYING OUT THE INVENTION

Figure 1:
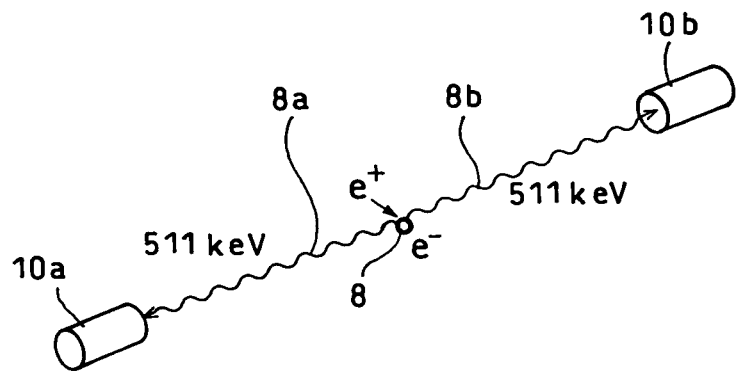
FIG. 1 is a drawing illustrating the principle of PET.
Figure 2:
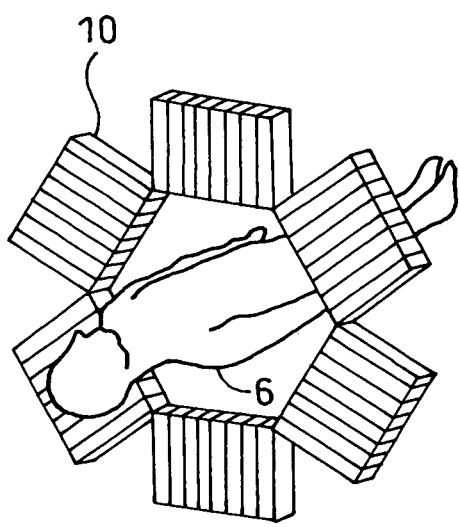
FIG. 2 is a perspective view illustrating one example of a conventional PET scanner.
Figure 2:
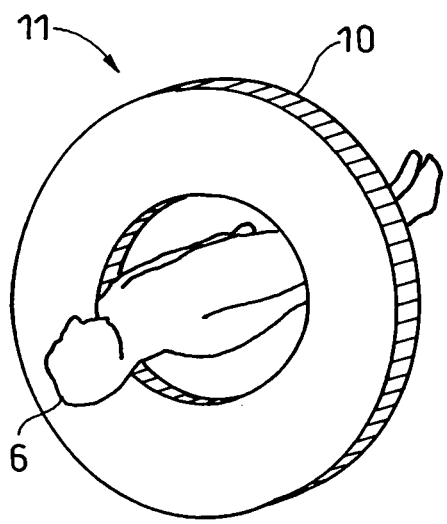
Figure 3:
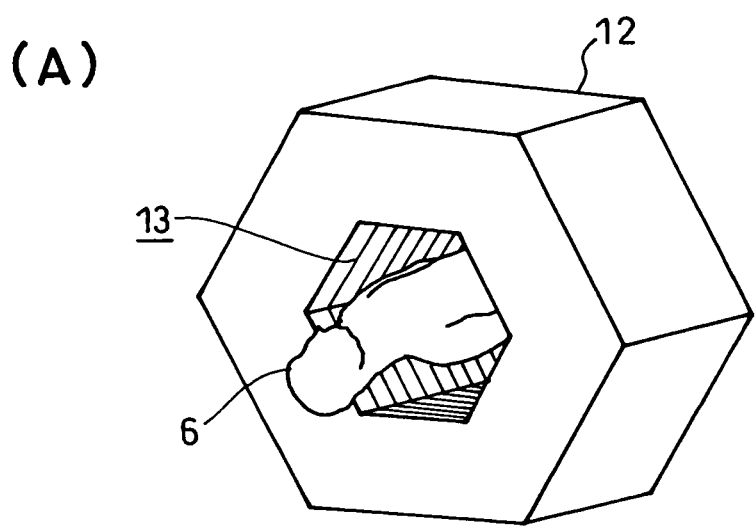
FIG. 3 is also a perspective view illustrating one example of a multi-ring PET scanner.
Figure 3:
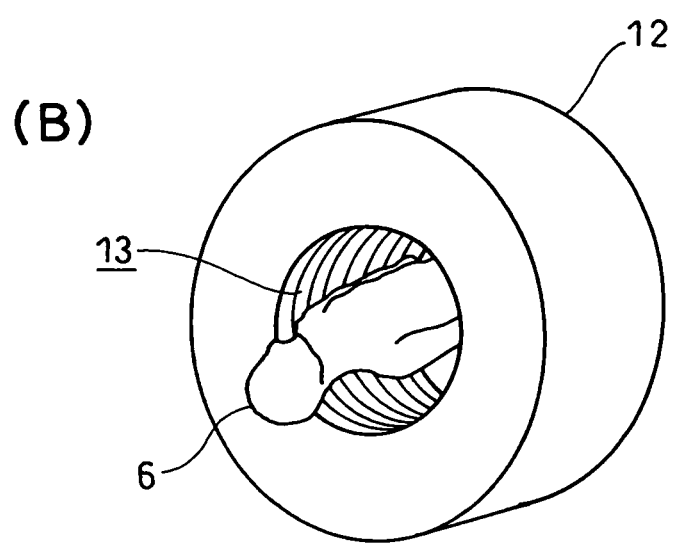
Figure 4:
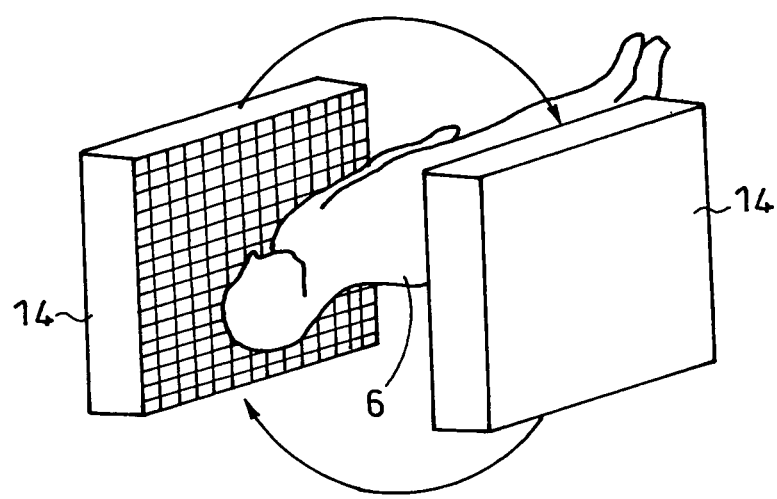
FIG. 4 is also a perspective view illustrating one example of a gamma-camera opposition-type PET scanner.
Figure 5:
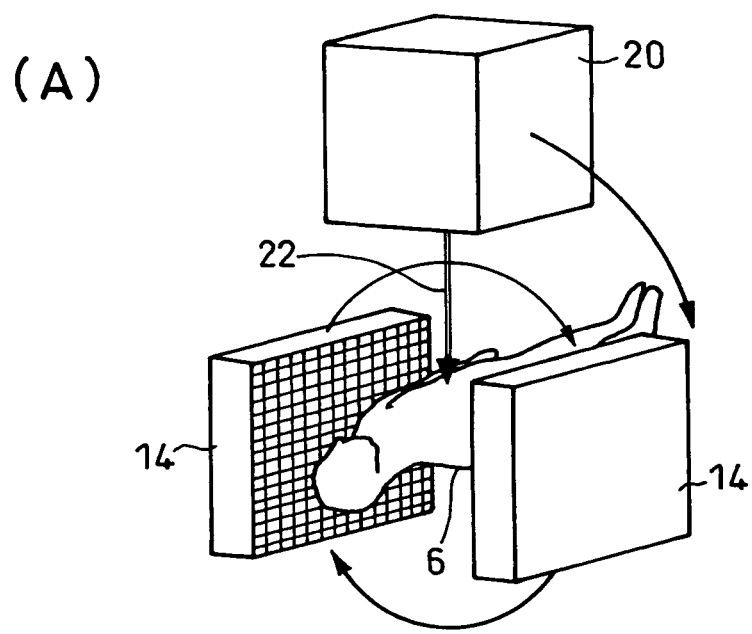
FIG. 5 is a perspective view illustrating a conventional structure of a PET scanner which monitors particle radiotherapy.
Figure 5:
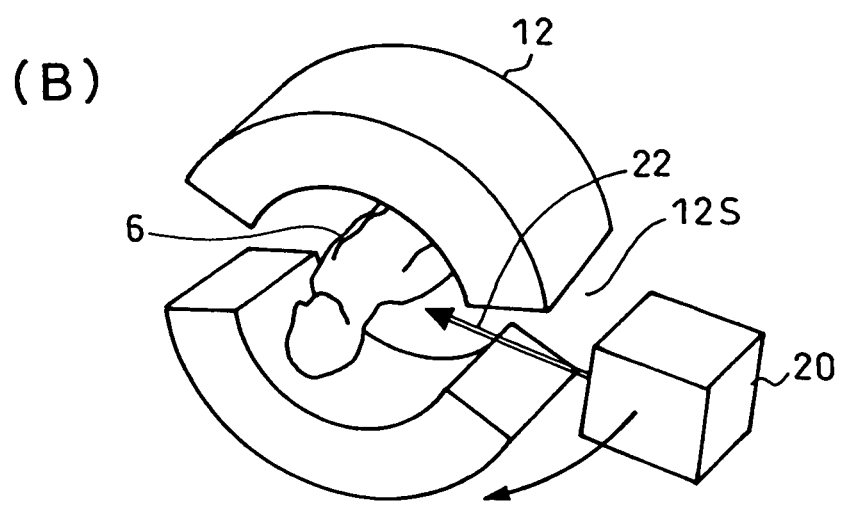
Figure 6:
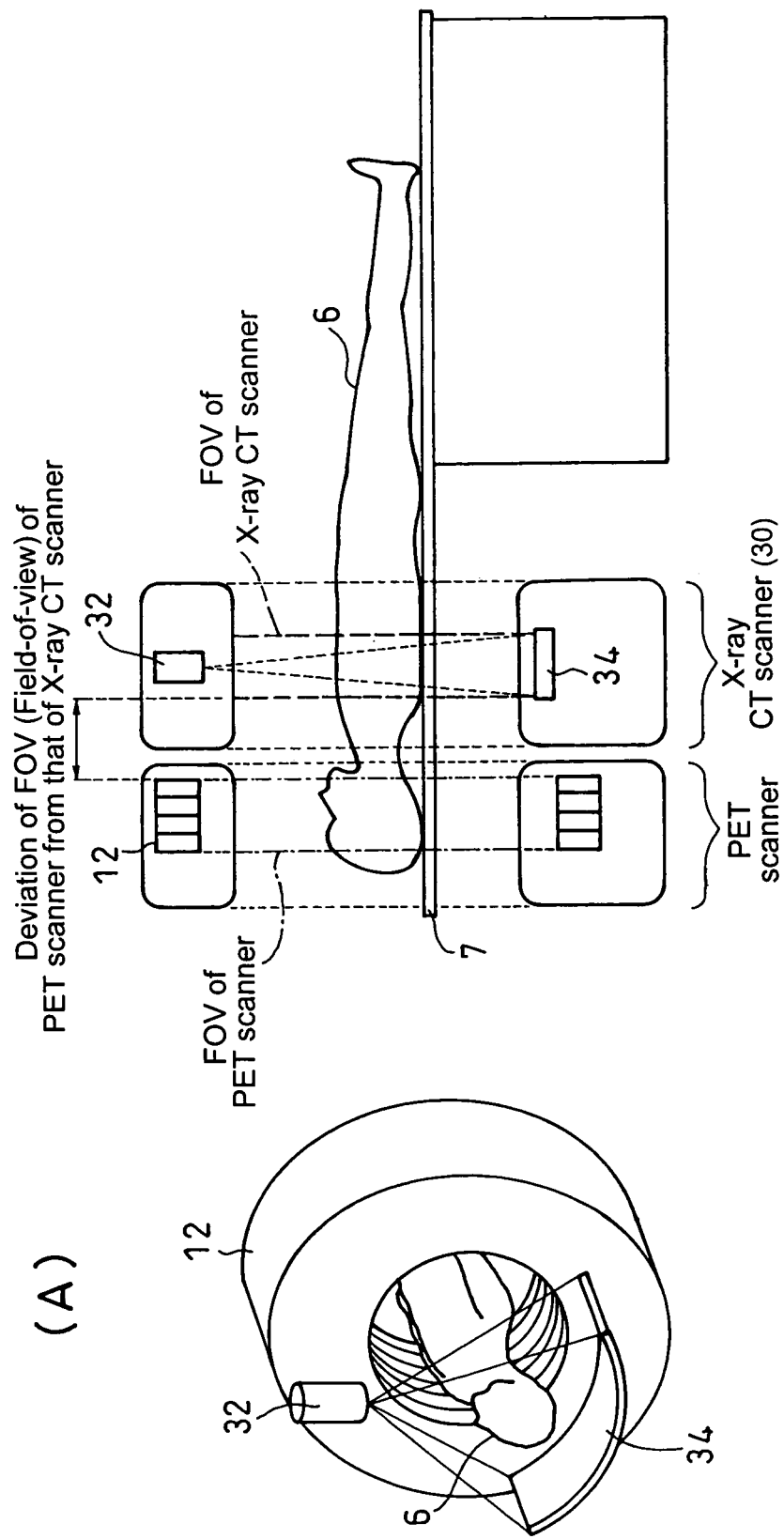
FIG. 6 (A) is a perspective view illustrating one example which illustrates a conventional PET/CT scanner and FIG. 6 (B) is a longitudinal sectional view thereof.
Figure 7:
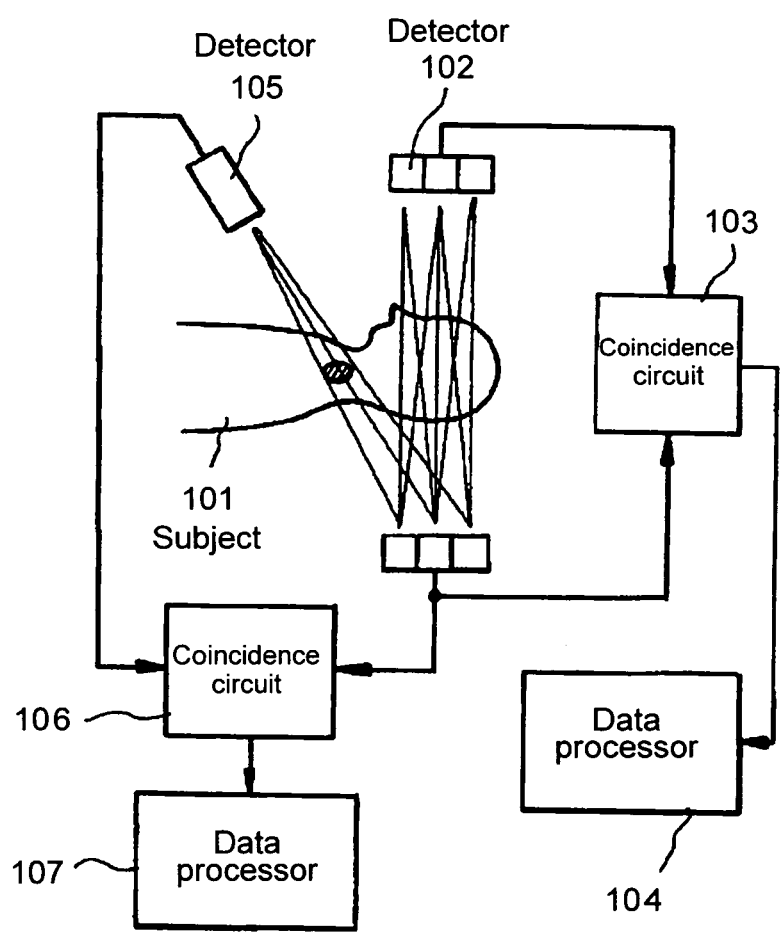
FIG. 7 is a block diagram of the equipment proposed in Japanese Published Unexamined Patent Application No. Hei 5-150046.
Figure 8:
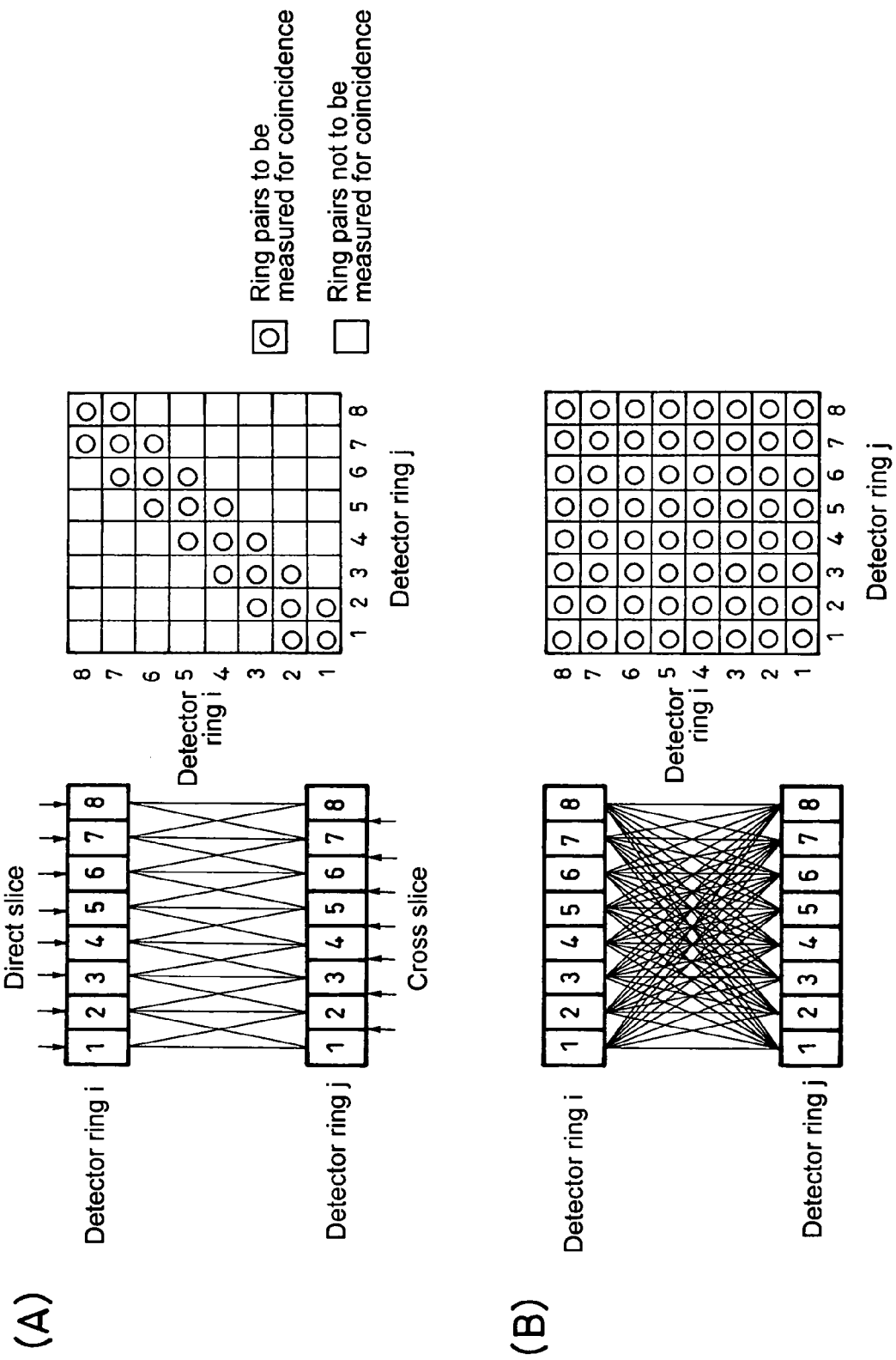
FIG. 8 (A) is a drawing illustrating the two-dimensional mode collection by a conventional PET scanner and FIG. 8 (B) is a drawing illustrating the three-dimensional mode collection.
Figure 9:
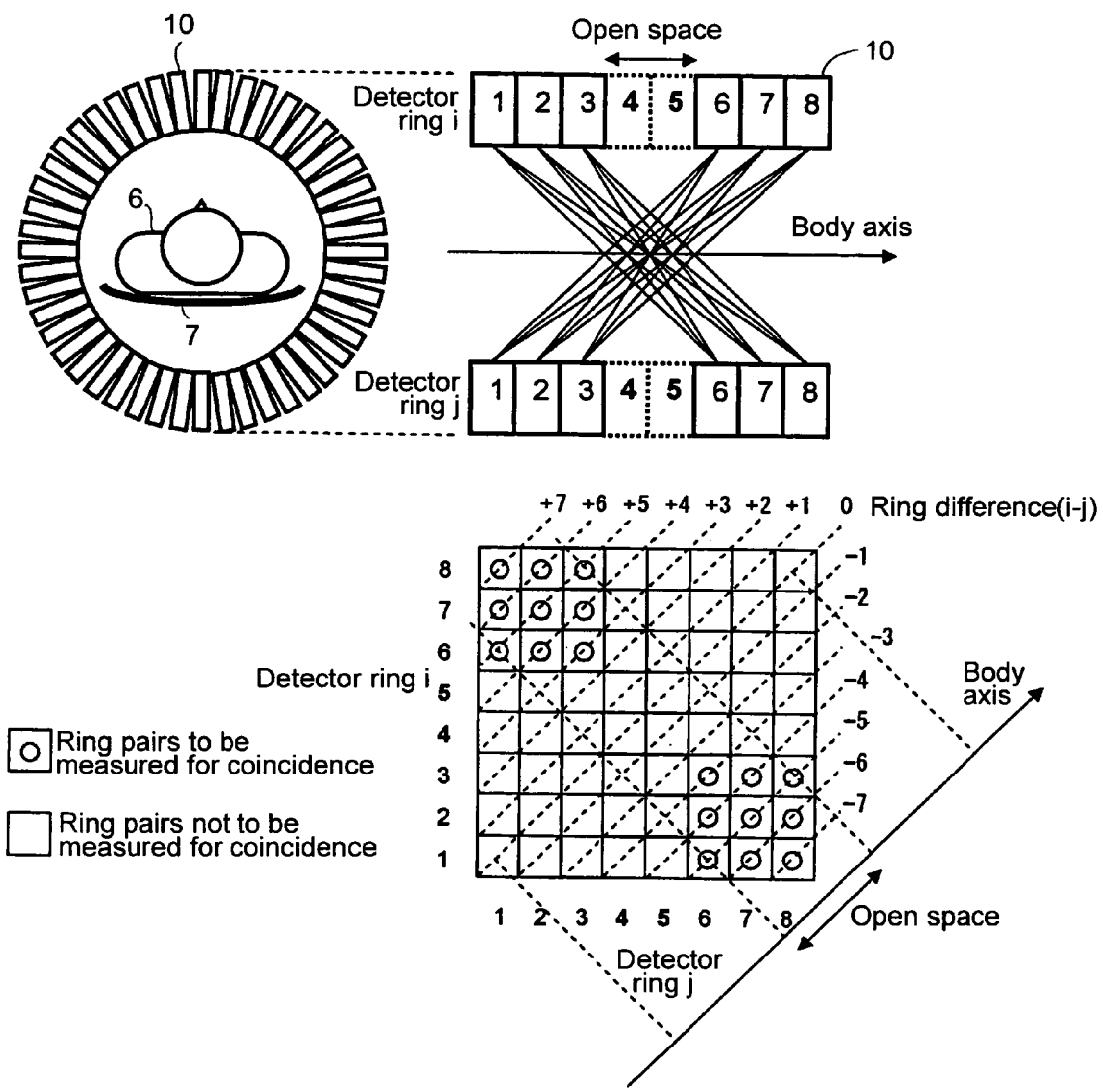
FIG. 9 is a drawing illustrating the principle of the present invention.

Hereinafter, a description will be given in detail for embodiments of the present invention by referring to the drawings.

Figure 10:
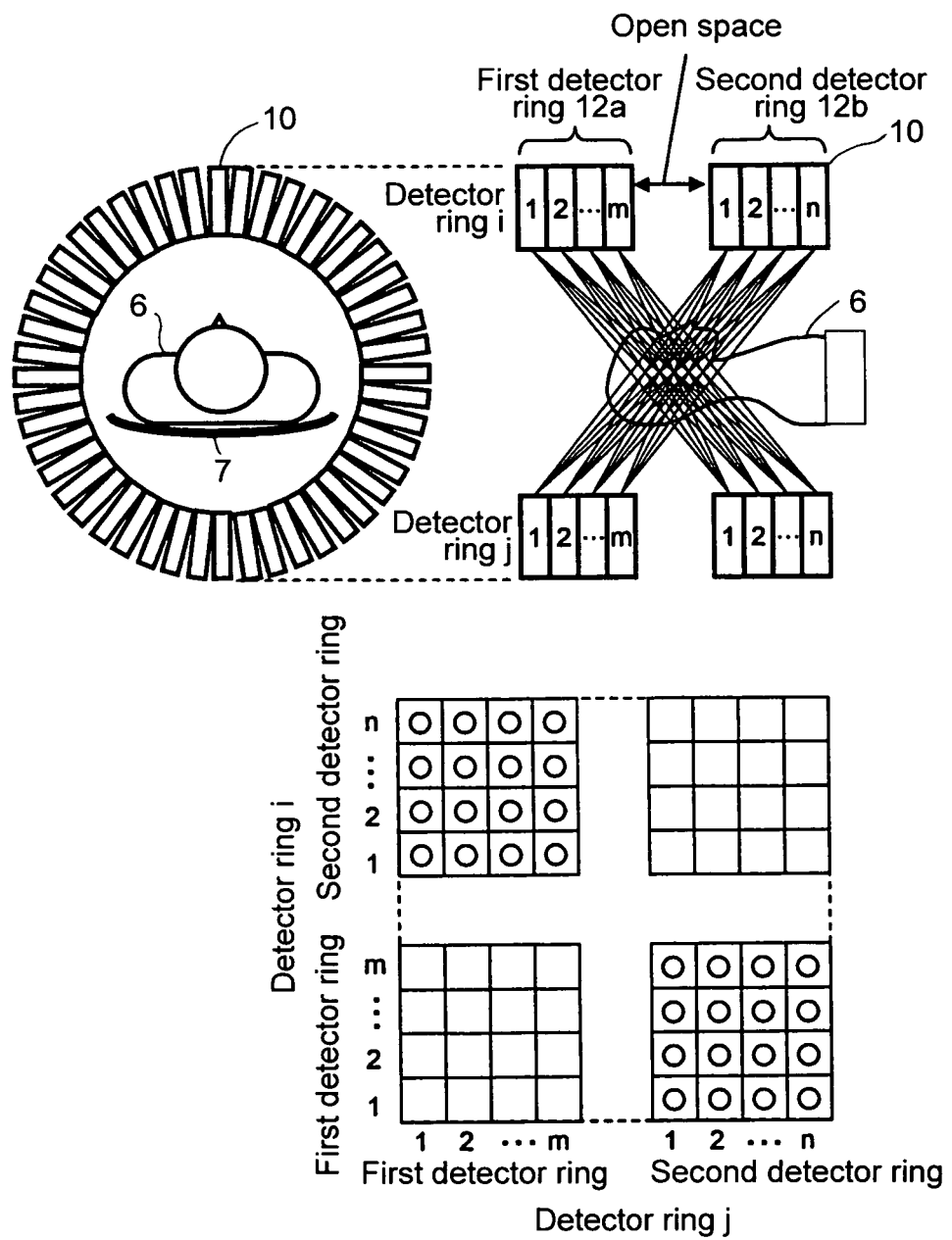
FIG. 10 is a drawing illustrating a constitution of a first embodiment of the present invention.

As shown in FIG. 10, in the first embodiment of the present invention, a first detector ring 12a and a second detector ring 12b in which detectors 10 arranged densely or spatially in a ring shape or in a polygonal shape are arranged, with an open space kept in the body axis direction, coincidences are measured for some of or all of detector pairs connecting the first detector ring 12a with the second detector ring 12b to perform three-dimensional image reconstruction, thereby imaging as a tomographic image an open space between the first detector ring 12a and the second detector ring 12b.

Figure 11:
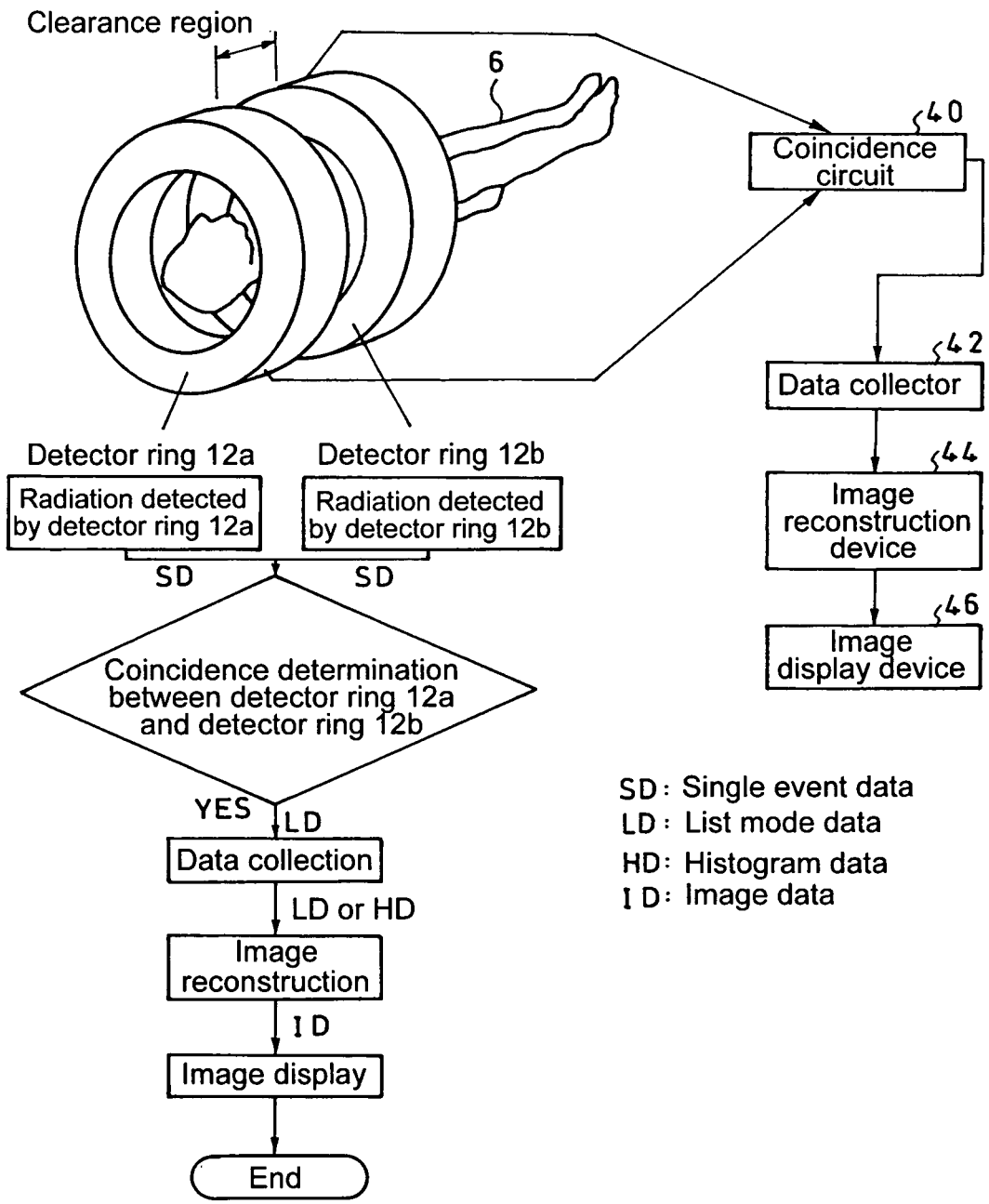
FIG. 11 is a flow chart illustrating procedures for obtaining tomographic images of a clearance region in the first embodiment.

FIG. 11 is a flow chart illustrating processing procedures in a constitution having two detector rings, that is, the detector ring 12a and the detector ring 12b.

For the sake of explanatory convenience, a region which is imaged as a tomographic image is divided into three regions, that is, a first FOV within the detector ring 12a, a second FOV within the detector ring 12b, and an open space (also referred to as a clearance region) between the detector rings 12a and the 12b.

In the detector rings 12a and 12b, when one radiation is detected, positional information of a detecting element which has detected the radiation, energy information of the radiation, and information of the thus detected time are taken out as single event data SD. This single event data SD is sent sequentially to a coincidence circuit 40, thereby determining coincidences between the single event data SD taken out respectively from the detector rings 12a and 12b. Then, the single event data SD is converted to list mode data LD, or information on a pair of detecting elements which have detected one pair of annihilation (gamma) photons. The list mode data LD is retained by a data collector 42 at a memory unit as it is. Alternatively, the list mode data LD is retained as histogram data HD at the memory unit, and thereafter image reconstruction device 44 is used to make image reconstruction calculation to obtain a tomographic image of the clearance region, thereby displaying it on an image display device 46.

On calculating the image reconstruction, an element $a_{ij}$ of a system matrix to be calculated or referred is defined as a probability in which annihilation radiation generated from a $j^{th}$ pixel of an image is determined as an $i^{th}$ coincidence line. As a method for calculating system matrix elements, several calculation methods such as a method based on the length of a line segment at which a coincidence line intersects with a pixel and a method using Monte Carlo simulation have been proposed. In either method, it is necessary to adjust the position coordinates of the detector to an actually used scanner.

Figure 12:
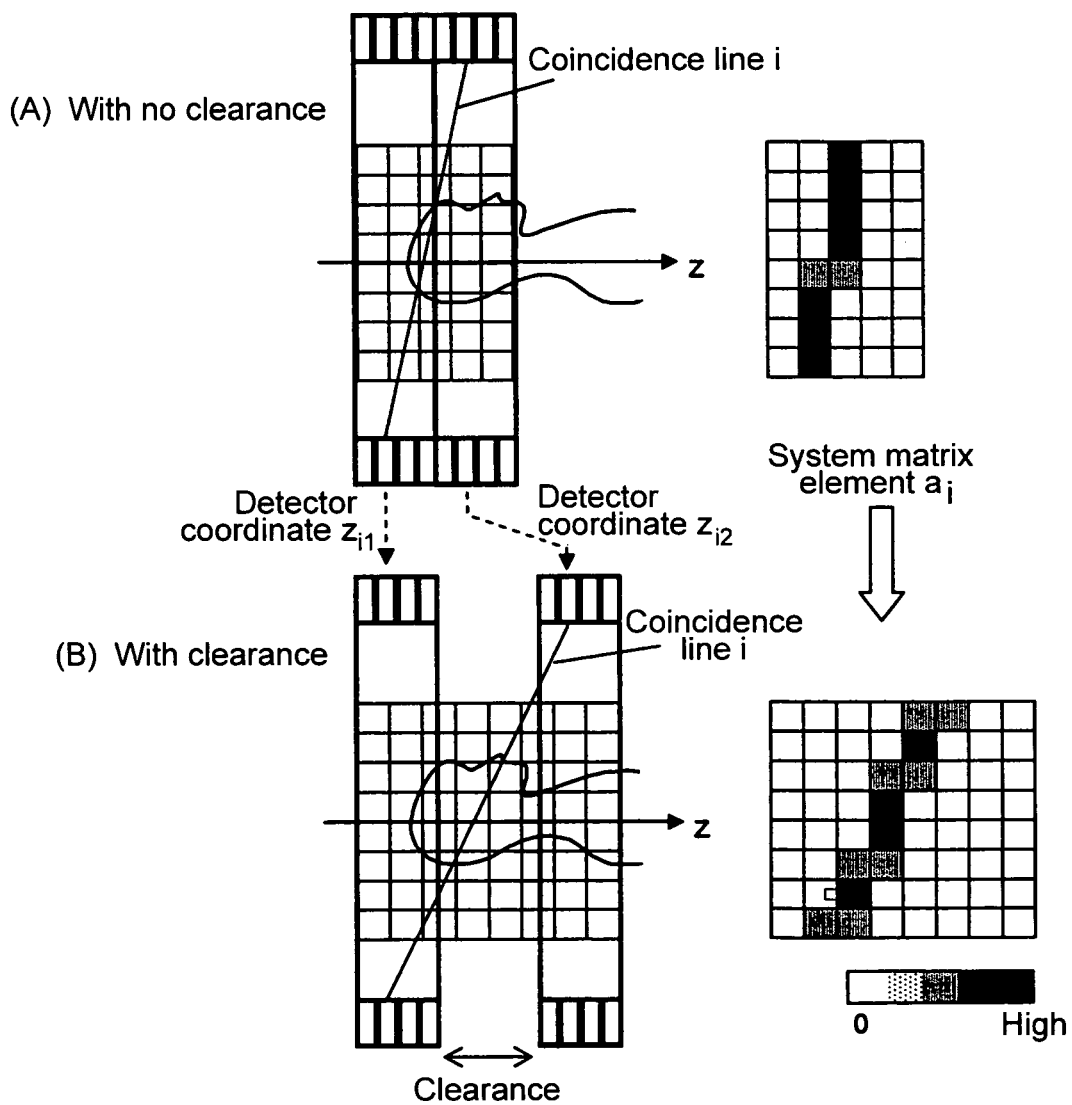
FIG. 12 is a drawing comparatively illustrating a system matrix where the clearance is absent and where it is present.

FIG. 12 illustrates an example of a system matrix by comparing a case of (A) where no clearance is provided and a case of (B) where a clearance is provided. When the detector coordinates of detector pairs corresponding to the coincidence line fare given respectively as $z_{i1}$ and $z_{i2}$, these coordinates of $z_{i1}$ and $z_{i2}$ are changed according to the movement of the detectors (in the example shown in FIG. 12, $z_{i1}$ is fixed and $z_{i2}$ is changed). Thereby, it is necessary to change the system matrix according to the change in detector coordinates.

Figure 13:
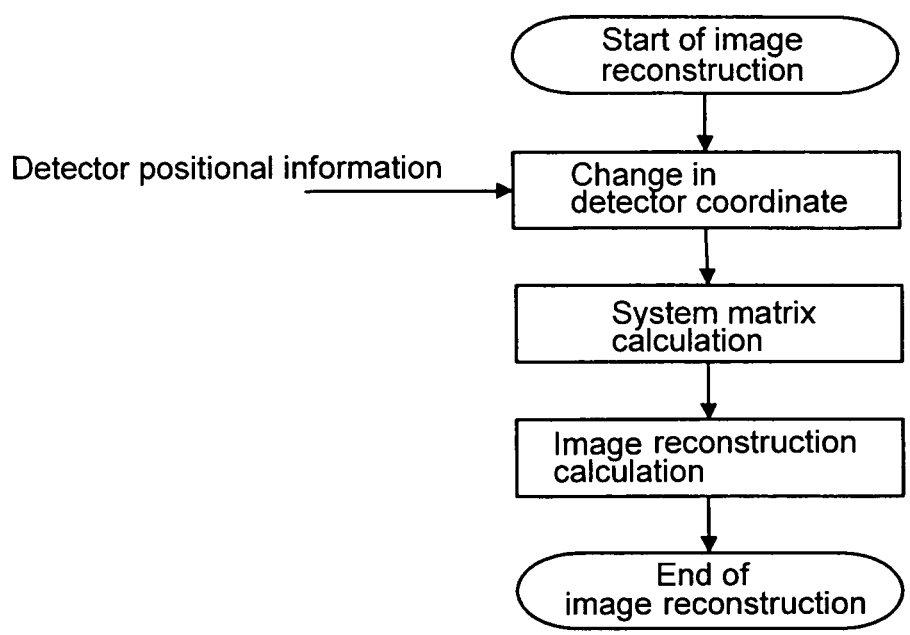
FIG. 13 is a flowchart illustrating procedures for calculating image reconstruction.

FIG. 13 is a flow chart illustrating procedures for calculating the image reconstruction in an image reconstruction device. On the basis of gantry positional information which is transmitted from a gantry position controller to the image reconstruction device 44 or accommodated inside list mode data LD, detector coordinates are changed. Then, system matrix elements are calculated according to the thus changed detector coordinates. A system matrix in the image reconstruction can be utilized by a method in which the elements are in advance calculated and retained and read sequentially on calculation of the image reconstruction and by a method in which on calculating the image reconstruction, the elements are sequentially calculated, whenever necessary.

Where detector rings are equal in diameter, the detector rings move in parallel and also move in a step width which is an integral multiple number with respect to the intervals of detectors in the body axis direction, mask processing is given to a system matrix which is defined for a virtual arrangement of detectors in which the detectors are continuously arranged with no clearance kept, thus making it possible to easily change the system matrix.

Figure 14:
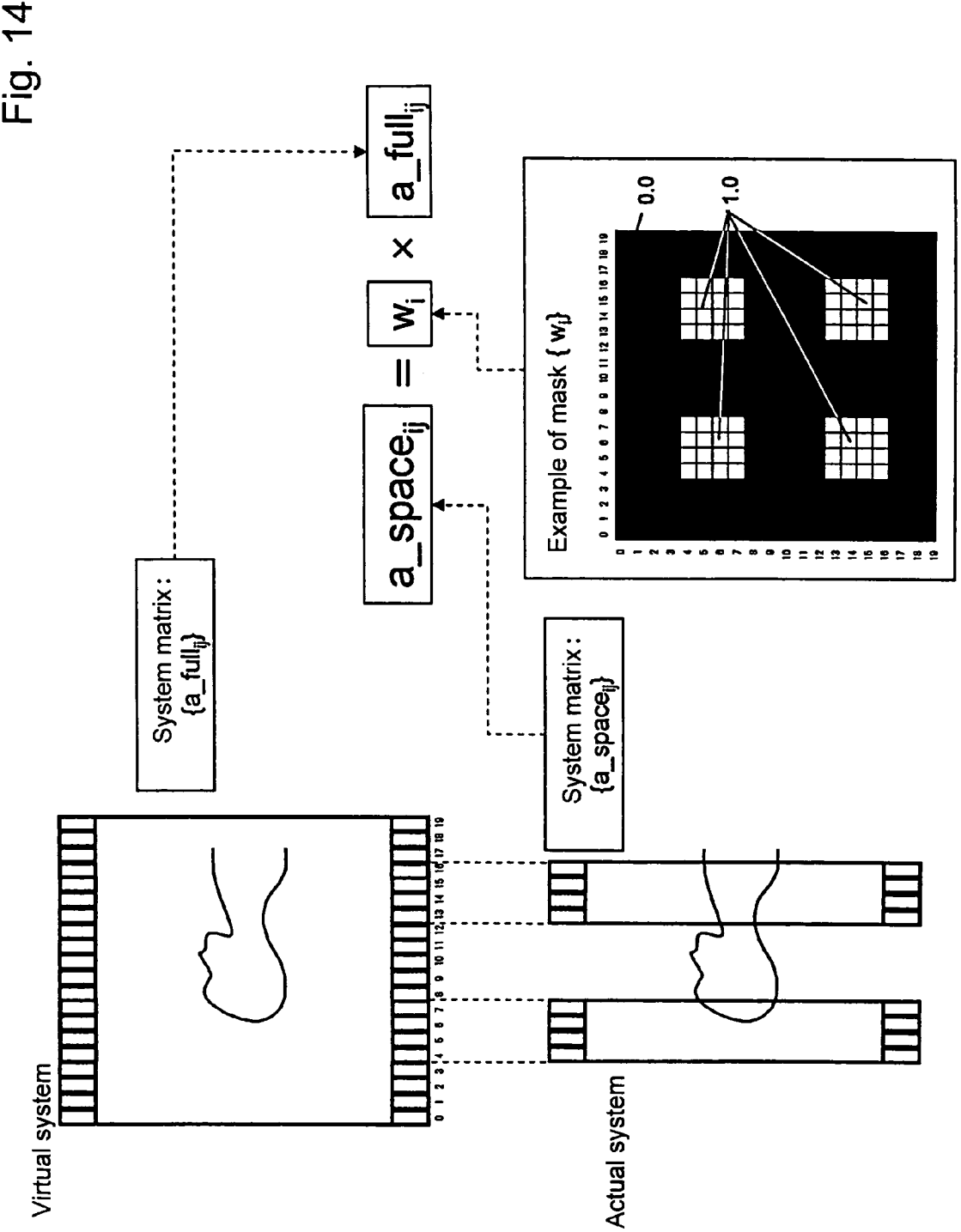
FIG. 14 is a drawing illustrating a modified example of the system matrix by mask processing.

Specifically, as illustrated in FIG. 14, a system matrix [a_full$_{ij}$] covering all the movement range of the detector rings is multiplied by a mask pattern [w$_i$] at which only a part where the detector rings are actually present is given as 1.0 and the rest is given as 0.0 according to the actual arrangement of the detector rings, thereby obtaining an actual system matrix {a_space$_{ij}$}.

Figure 15:
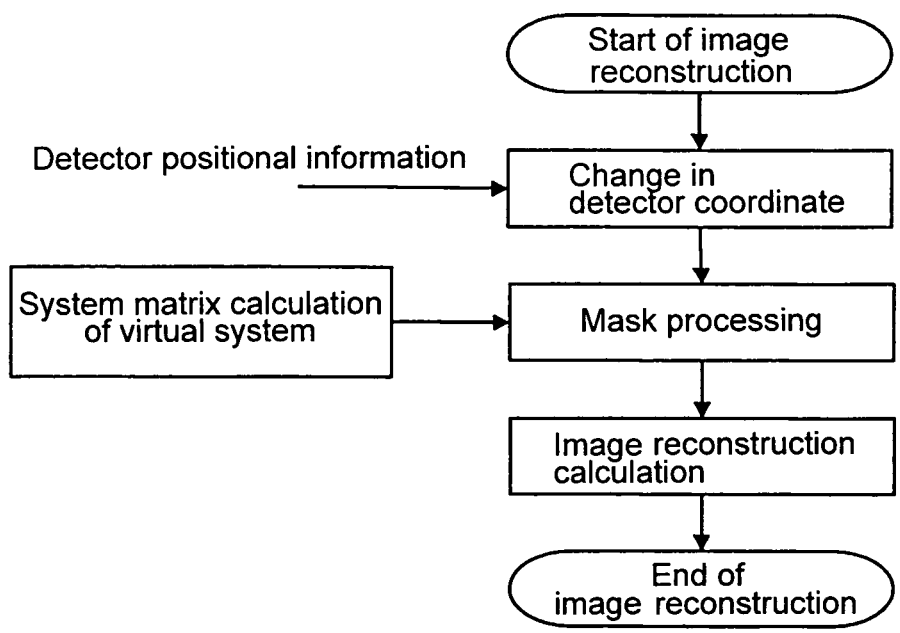
FIG. 15 is a flow chart illustrating procedures for the method given in FIG. 14.

FIG. 15 is a flow chart illustrating procedures for calculating the image reconstruction by the method given in FIG. 14. Mask processing by a mask prepared according to change in detector coordinates is given to the system matrix of a virtual system. The system matrix calculation of a virtual system is subjected to calculation/retention in advance or may be sequentially calculated, whenever necessary, on calculation of the image reconstruction.

As described so far, where the length of an open space between detector rings is an integral multiple number with respect to the size of the detector ring, it is possible to easily perform the reconstruction calculation. In addition, the length of the open space shall not be limited to an integral multiple number with respect to the detector ring.

Figure 16:
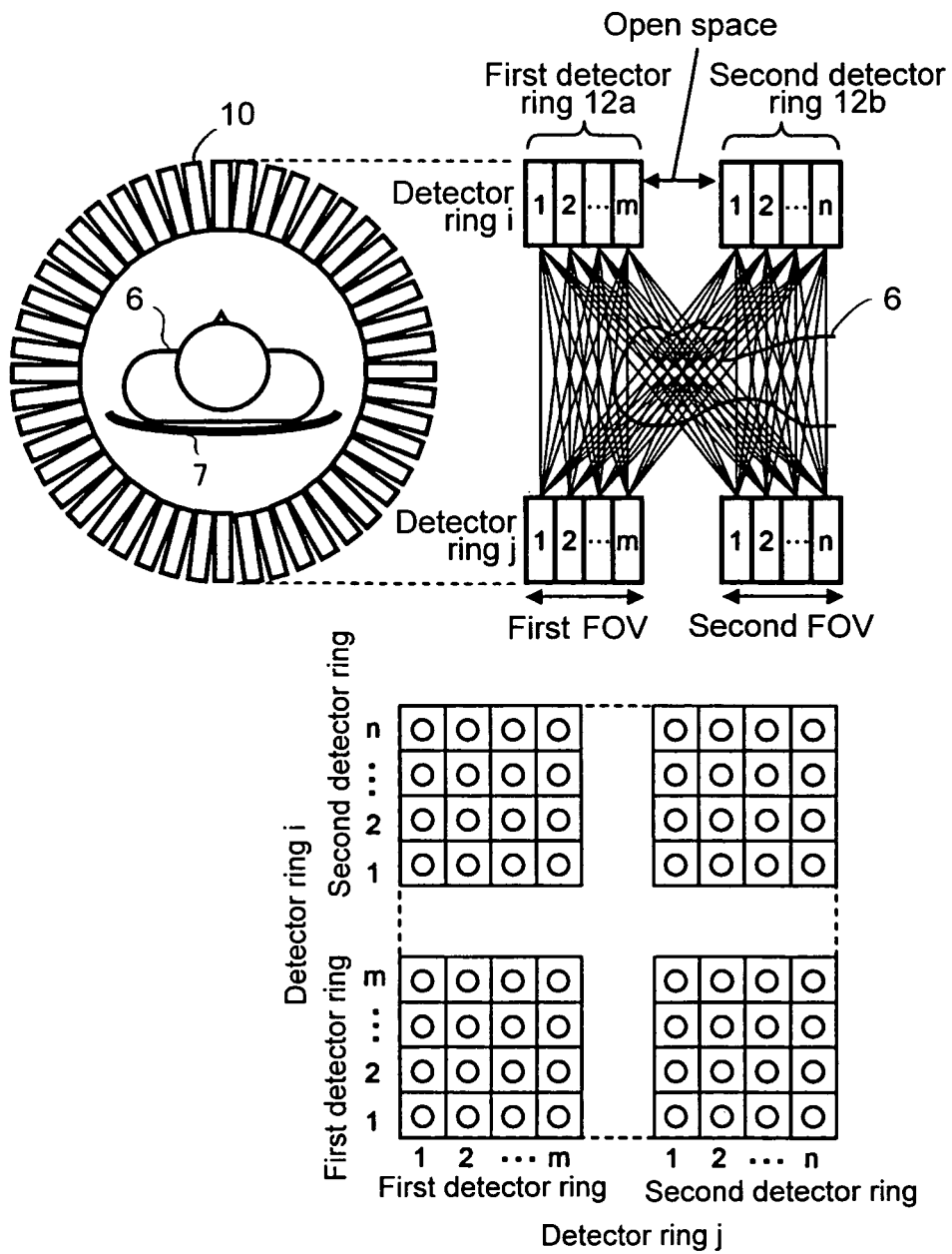
FIG. 16 is a drawing illustrating a constitution of a second embodiment of the present invention.

Next, a description will be given in detail for the second embodiment of the present invention by referring to FIG. 16.

The present embodiment is a PET scanner similar to that of the first embodiment, in which not only coincidences are measured for some of or all of detector pairs connecting a first detector ring 12a and a second detector ring 12b but also coincidences are measured for some of or all of detector pairs within the first detector ring 12a and some of or all of detector pairs within the second detector ring 12b to perform the three-dimensional image reconstruction. Thereby, a continuous region which combines a first FOV of the first detector ring 12a, a second FOV of the second detector ring 12b and an open space is imaged as tomographic images.

Figure 17:
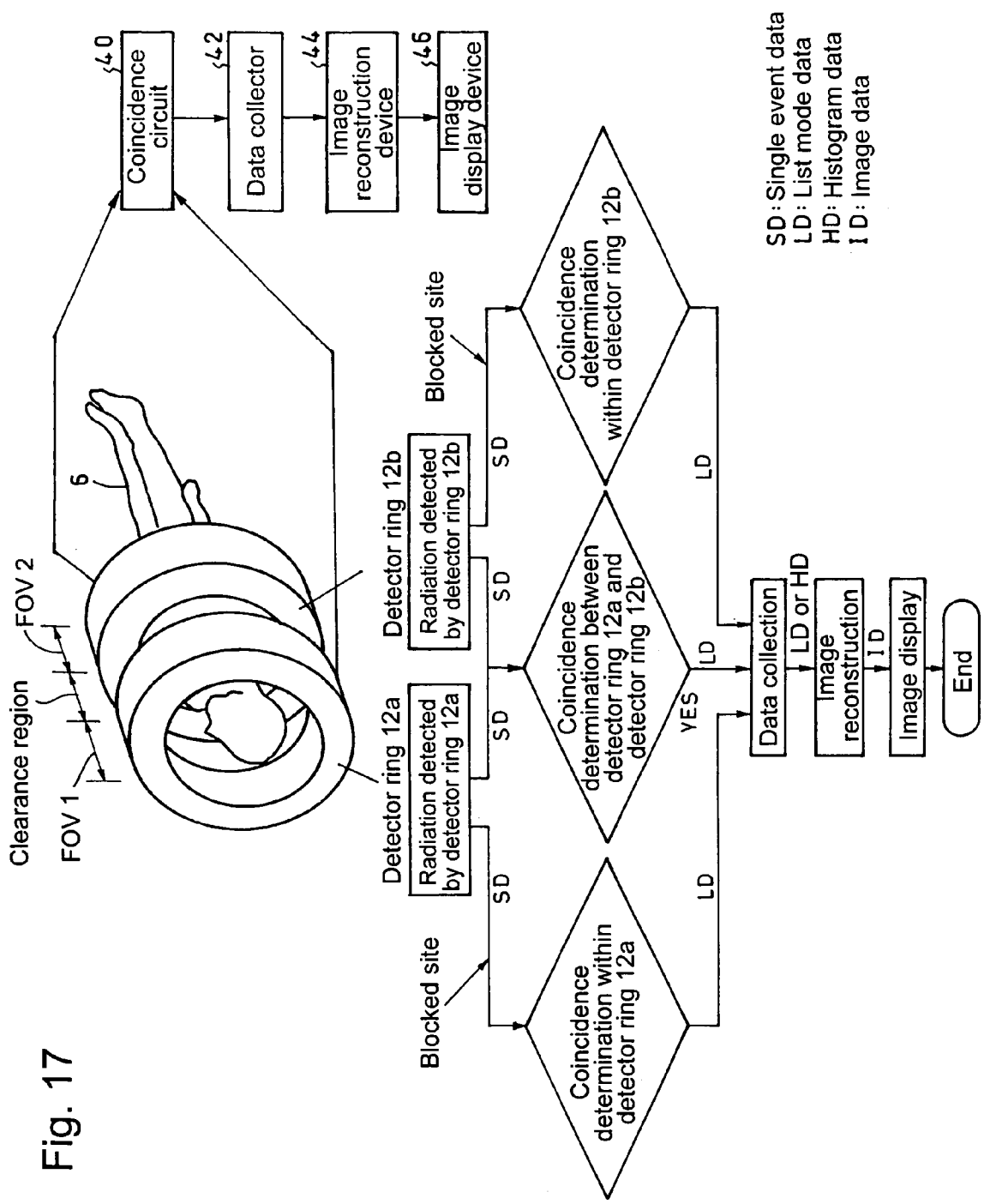
FIG. 17 is a flow chart illustrating procedures for obtaining tomographic images in the second embodiment.

FIG. 17 illustrates procedures for obtaining tomographic images which combine the clearance region, the first FOV and the second FOV in the second embodiment. Coincidences are determined within the detector ring 12a and within the detector ring 12b, in addition to the coincidences determined between the detector rings 12a and 12b. The thus obtained list mode data LD is combined by the data collector 42 and converted to a mass of list mode data LD or histogram data HD. Then, the image reconstruction device 44 is used to perform image reconstruction, thus making it possible to obtain tomographic images at a continuous FOV which combines the clearance region, the first FOV and the second FOV.

The procedures given in FIG. 17 are able to remove unnecessary single event data SD from a data stream by blocking signals at two sites given in this drawing where only the clearance region may be imaged, thus making it possible to easily improve throughput and expand a dynamic range. However, the procedures are complicated in system constitution.

Figure 18:
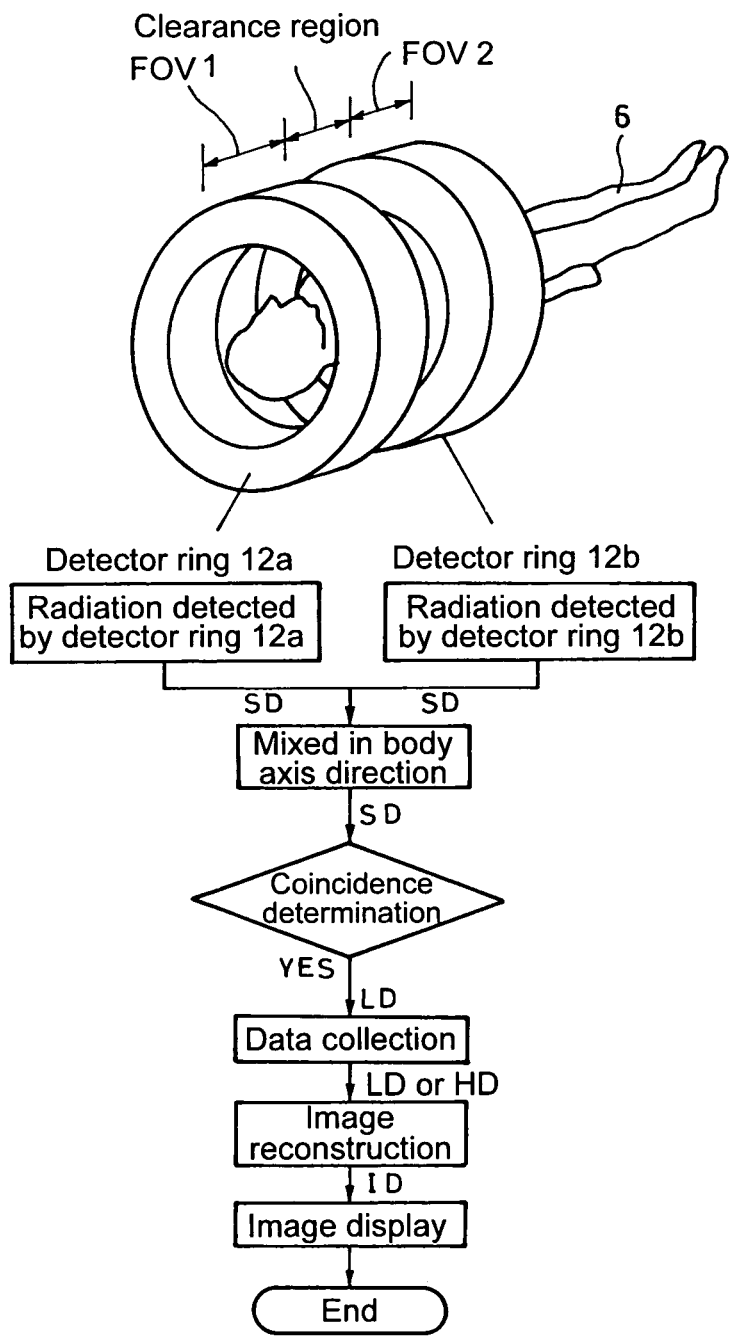
FIG. 18 is a drawing illustrating a simplified example given in FIG. 17.
Figure 19:
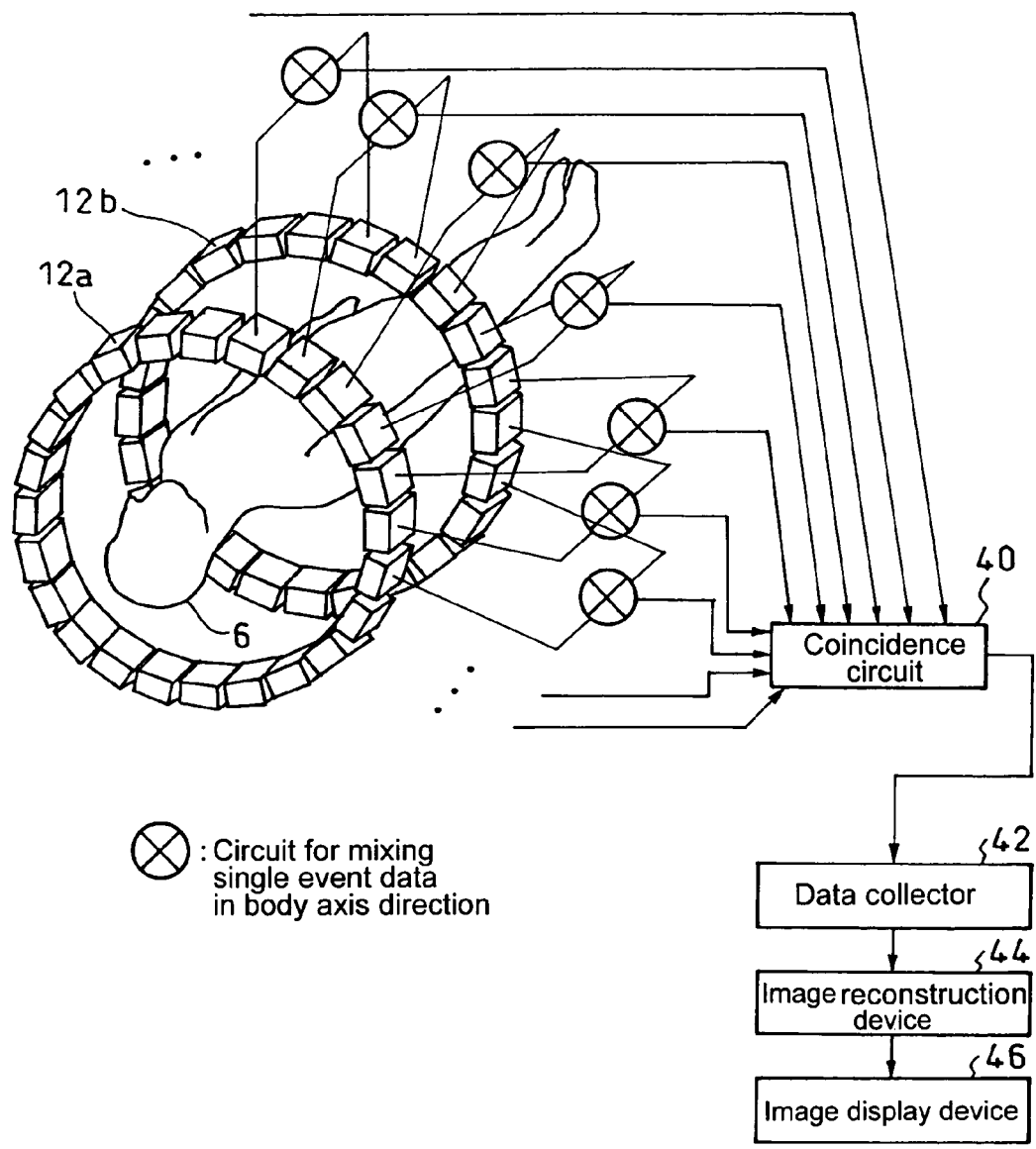
FIG. 19 is a block diagram corresponding to FIG. 18.

FIG. 18 illustrates procedures for simplifying the constitution given in FIG. 17. In FIG. 18, at a stage prior to coincidence determination, after the single event data SD is mixed in the body axis direction, coincidences are to be determined at one site. Since the thus mixed single event data SD includes data resulting respectively from the detector rings 12a and 12b, coincidences determined at one site are referred to determine coincidences within the detector ring 12a, within the detector ring 12b, and at a clearance between the detector rings 12a and 12b. FIG. 19 illustrates a block diagram corresponding to FIG. 18.

In the first and second embodiments, there is only power cable s and signal cable s which are needed to be physically present laid between the first detector ring 12a and the second detector ring 12b. Therefore, a gantry in itself is completely or partially separated, by which an open space can be secured for gaining access to a patient from outside the gantry.

In addition, in the first and the second embodiments, the first detector ring 12a is equal in size to the second detector ring 12b. However, as illustrated in the third embodiment given in FIG. 20, the ring diameter is changed, for example, the first detector rings 12a corresponding to the head may be made smaller in diameter than the second detector ring 12b corresponding to the torso.

Figure 20:
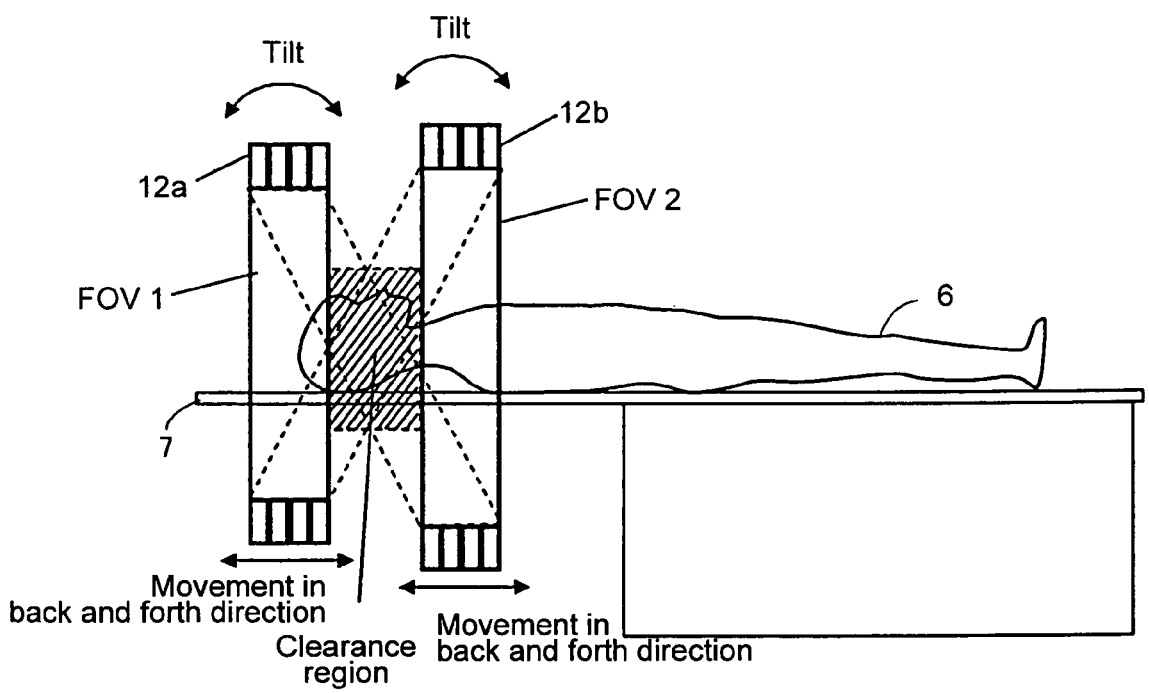
FIG. 20 is a drawing illustrating a third embodiment of the present invention.
Figure 21:
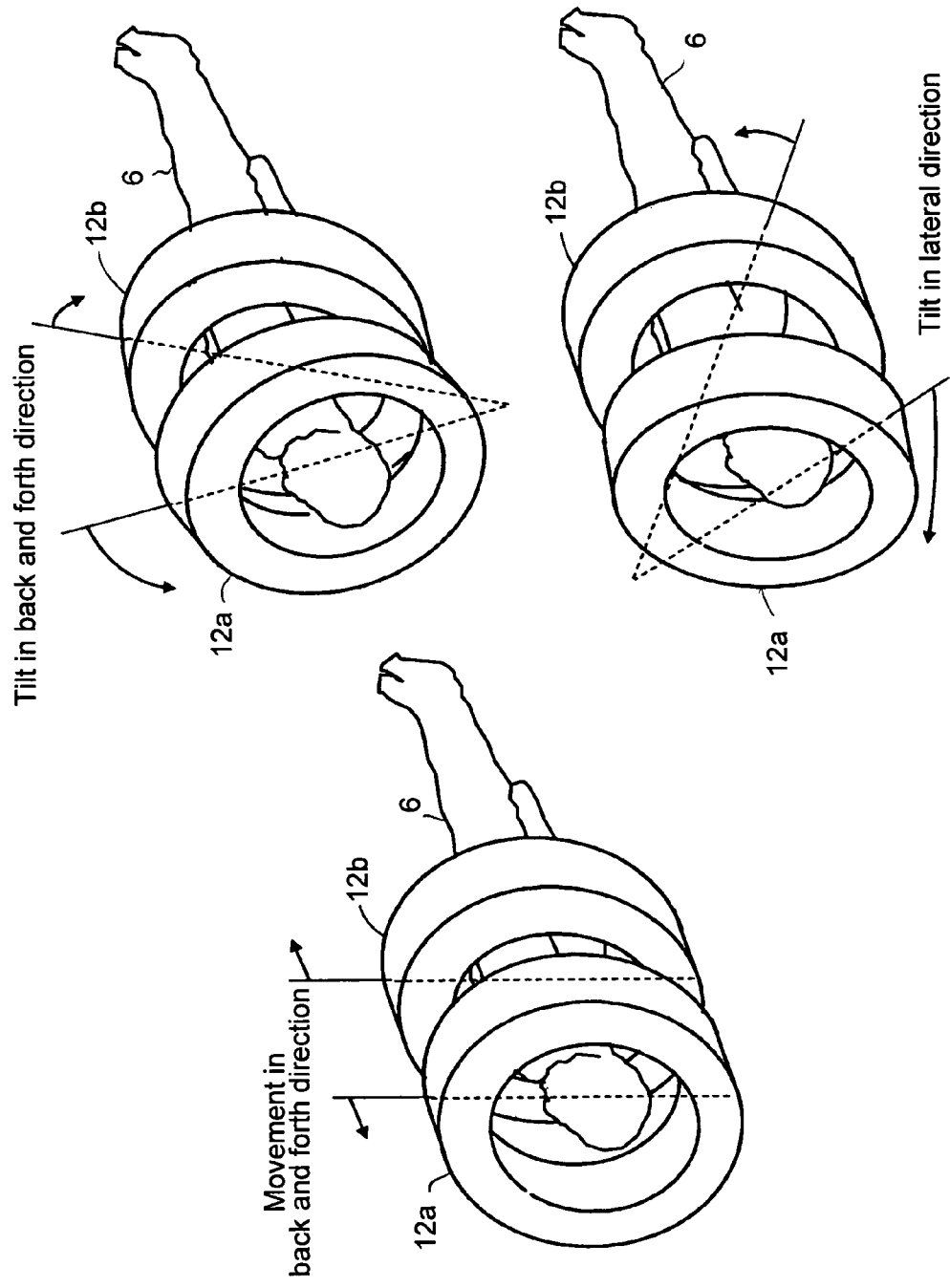
FIG. 21 is a perspective view illustrating an example of movement states of detector rings.

In addition, the positional relationship between separated detector rings may be fixed. However, since a greater clearance will inevitably result in the deteriorated quality of an image, it is desirable to adjust the size of the clearance, whenever necessary. As illustrated in FIG. 20 and FIG. 21, it is also desirable that each of the thus separated detector rings is structured so as to tilt in the back and forth direction and in the lateral direction, so as to move in the back and forth direction, or structured in a combined manner and that the clearance of the detector rings in the body axis direction can be changed according to the purpose of the check-ups or others. Further, detector rings are arranged so that no clearance is kept between them and can be used as an ordinary PET scanner.

Figure 22:
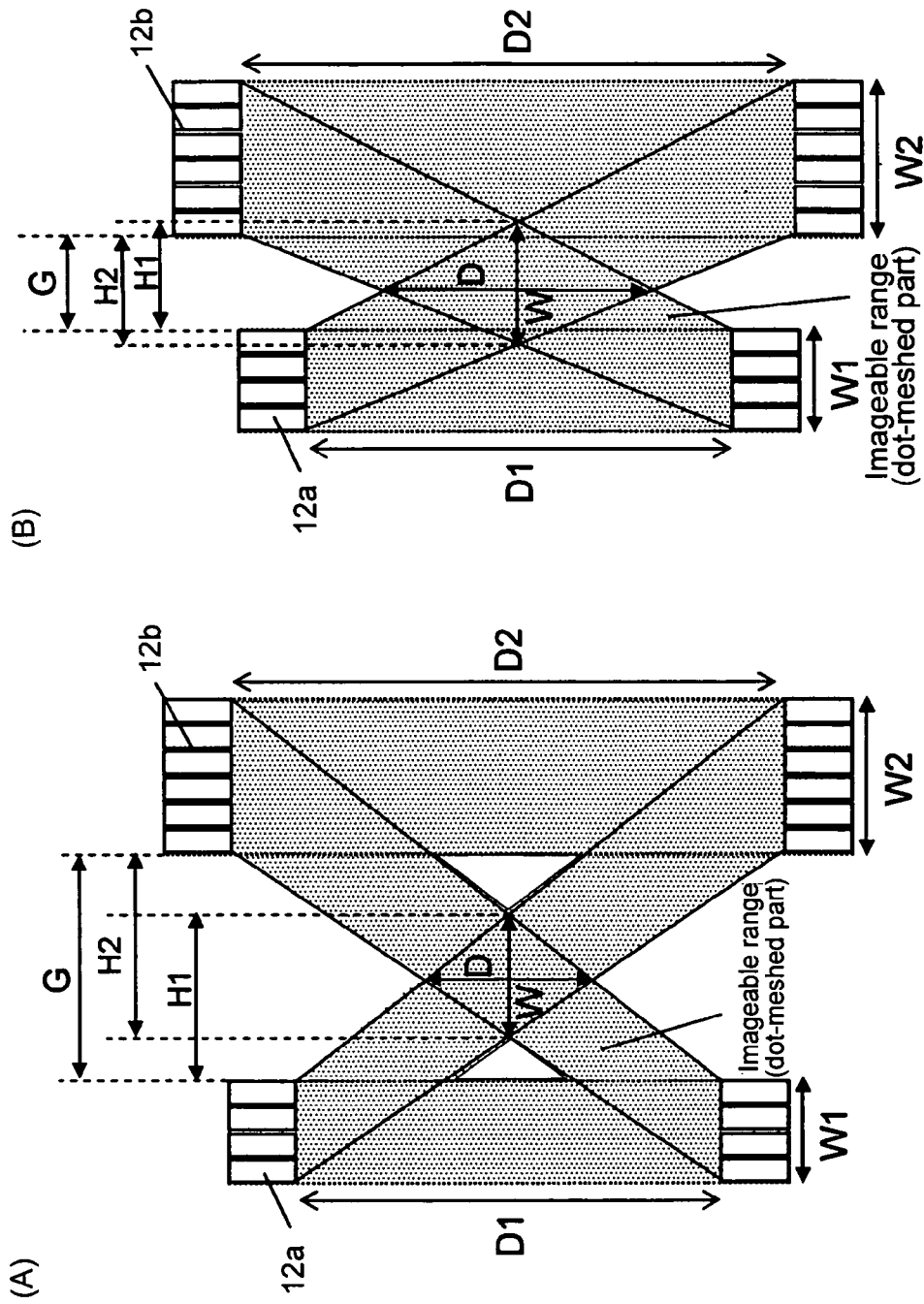
FIG. 22 is a drawing illustrating a method for calculating an allowable range in which the detector rings may be arranged.

In the third embodiment, allowable ranges between the first FOV, the second FOV, and the clearance region can be obtained as illustrated in FIG. 22. Specifically, when the ring diameter of the first detector ring 12a is given as D1, the width of the sensitivity area in the body axis direction is given as W1, the ring diameter of the second detector ring 12b is given as D2, the width of the sensitivity area in the body axis direction is given as W2, and the clearance between detector rings is given as G, following formulae can be used to calculate W, H1 and H2 in the drawing.

$$W=(D1\times W2+D2\times W1)/(D1+D2) \quad (1)$$

$$H1=D1\times(G+W2)/(D1+D2) \quad (2)$$

$$H2=D2\nu(G+W1)/(D1+D2) \quad (3)$$

Then, where the relationship of H1>W or H2>W or G>W is satisfied, as illustrated in FIG. 22 (A), a region is developed that is not imaged, by which a FOV in the body axis direction is made discontinuous. Therefore, as illustrated in FIG. 22 (B), in order to secure a FOV which is continuous in the body axis direction, it is necessary to arrange the detector rings and a clearance between the rings adjustably so as to attain the relationship of H1≤W, H2≤W, and G≤W. In FIG. 22, D is the diameter of a minimum FOV and can be calculated by the following formula.

$$D=D1\times D2\times W/(D1\times H2+D2\times H1) \quad (4)$$

Figure 23:
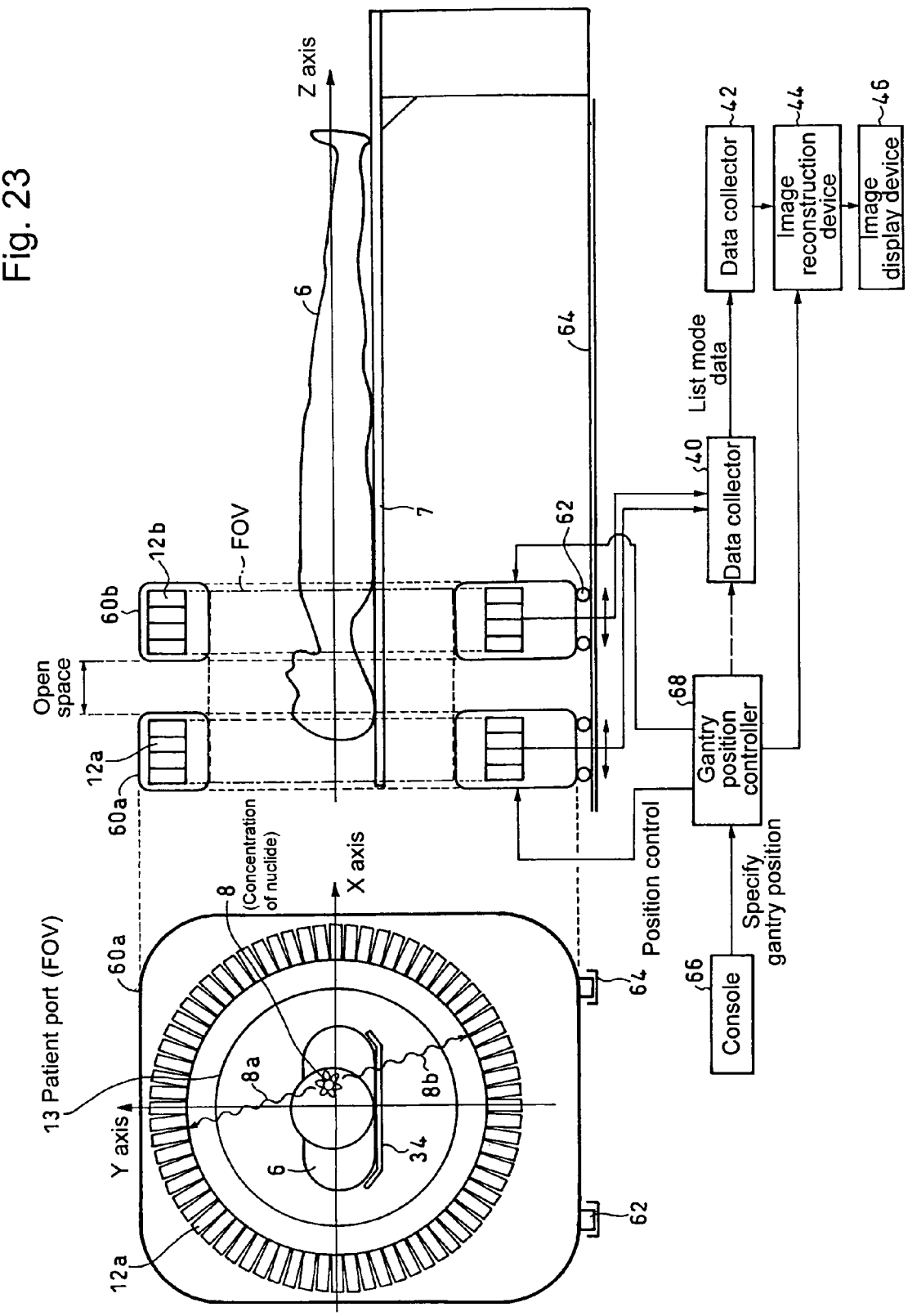
FIG. 23 is a drawing illustrating a first example of the present invention.

It is necessary to arrange the detector rings and a clearance between the rings adjustably so that the D value can be made greater than an examination target region to be imaged FIG. 23 illustrates a first example which has realized the first and the second embodiments. This example is constituted so that two identical detector rings 12a, 12b formed in a ring-shape are arranged in tandem as an independent gantry to make variable a clearance between the detector rings.

Specifically, the example is constituted with the detector rings 12a, 12b, gantry covers 60a, 60b for respectively covering them, and a bed 7 on which a patient 6 lies. A wheel 62 is mounted on each of the gantries and able to move them on a common or a separate rail 64 in the back and forth direction.

When the FOV is deviated in the body axis direction, the detector rings 12a and 12b are moved with respect to a fixed bed, or the detector rings 12a and 12b are fixed and the bed 7 is moved.

One pair of annihilation (gamma) photons 8a, 8b which travel approximately at an angle of 180° are emitted in all directions from a nuclide 8 concentrated inside the body of the patient 6. In the detector rings 12a and 12b, single event data SD which is measured data on one side of the pair annihilation (gamma) photons 8a, 8b is sent to a common coincidence circuit 40 and converted to list mode data LD, which is information on coincidence pairs, within the detector ring 12a, within the detector ring 12b, and between the detector rings 12a and 12b.

The list mode data LD is stored by the data collector 42 at a recording medium, thereafter sent to the image reconstruction device 44 and subjected to calculation of image reconstruction. Then, the image display device 46 is used to display a reconstruction image.

An open space can be secured for a patient by a clearance between the detector rings 12a and 12b. However, when the clearance between the detector rings is made greater, the deteriorated quality of an image is inevitably found. Therefore, it is desirable to adjust the size of the clearance to a minimum extent, depending on the necessity of check-ups. The detector rings 12a and 12b are controlled for the movement by the gantry position controller 68 on the basis of gantry positional information specified by a console device 66. The gantry positional information is included in the list mode data LD through the coincidence circuit 40 or directly sent to the image reconstruction device 44, thereby calculation can be made on calculation of image reconstruction based on the positional information of actual detectors.

Figure 24:
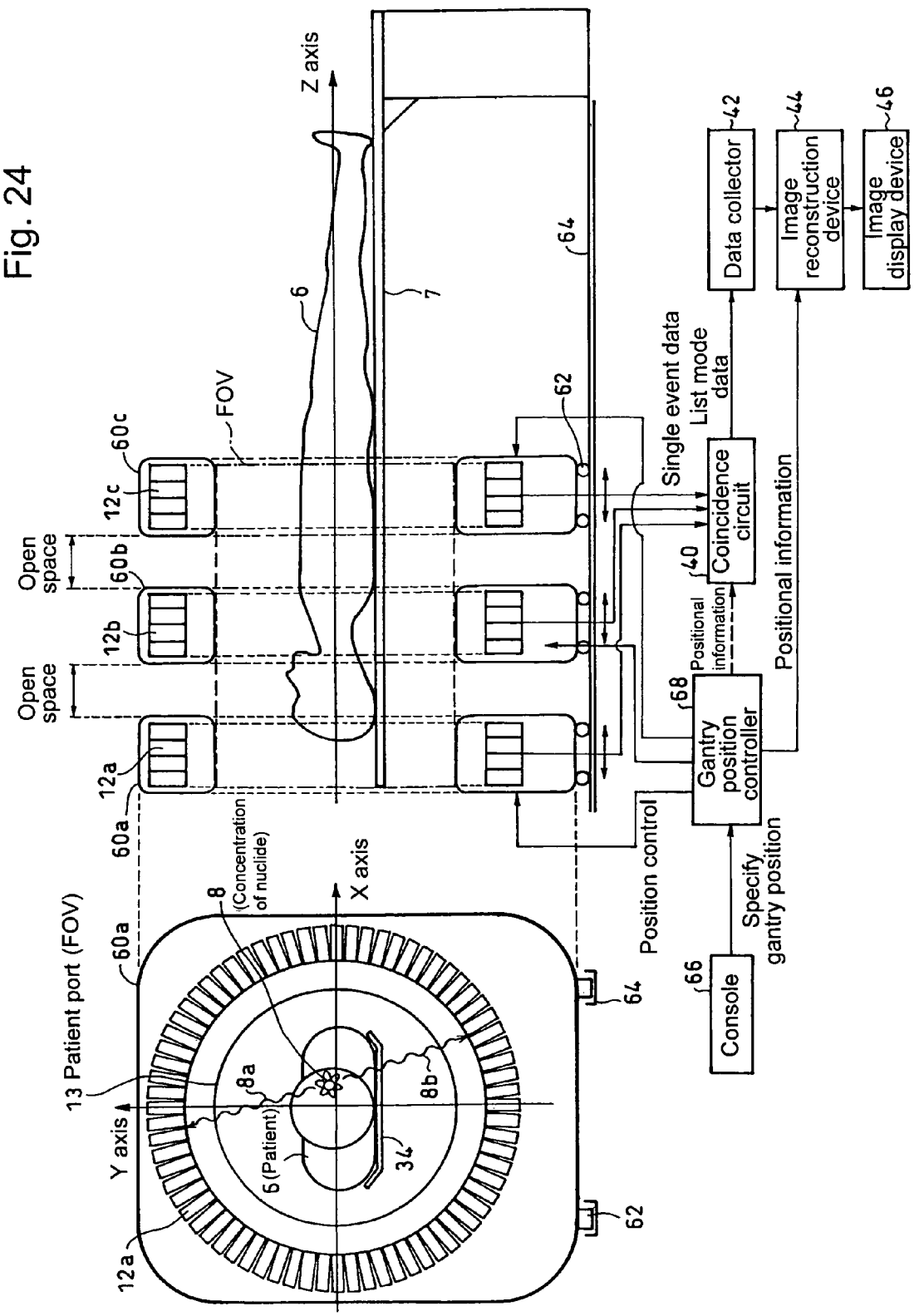
FIG. 24 is a drawing illustrating a second example of the present invention.

In the first example, there is provided two detector rings, for which the number of detector rings shall not be, however, limited. FIG. 24 illustrates a constitution of the second example in which three detector rings, 12a, 12b and 12c are arranged to provide an open space at two sites. In this drawing, the numeral 60c depicts a gantry cover of the detector ring 12c.

Figure 25:
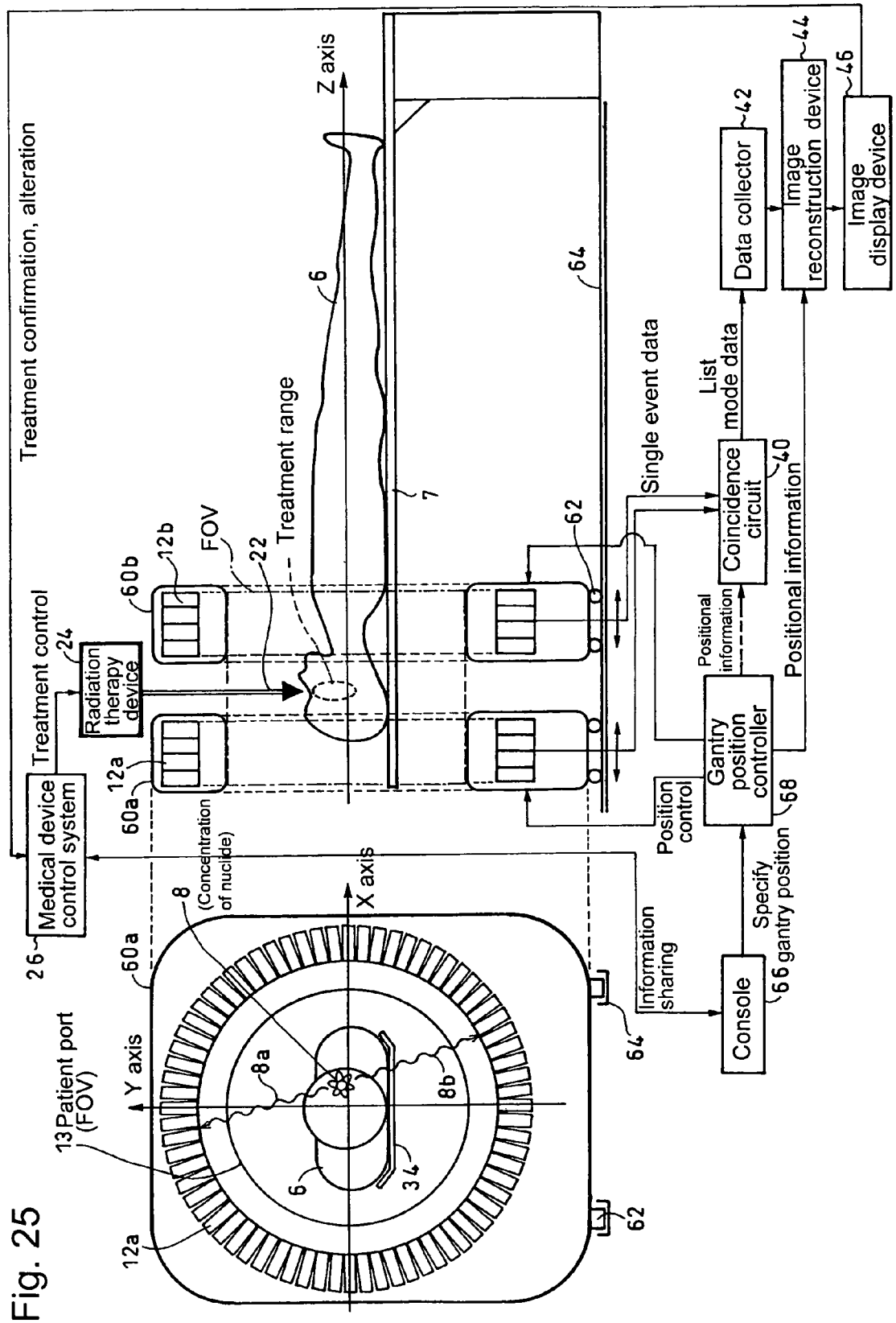
FIG. 25 is a drawing illustrating a third example of the present invention.

FIG. 25 illustrates a constitution of the third example of a PET scanner in which medical devices such as a radiation irradiation device 24 are inserted into a clearance region between the detector rings 12a and 12b, in a PET scanner in which two identical detector rings 12a, 12b formed in a ring shape are arranged in tandem as independent gantries (60a, 60b), and a clearance between the detector rings 12a and 12b is made variable, thereby providing treatment and monitoring the treatment to confirm the same site during the same session by PET.

Particle beams 22 generated from the radiation therapy device 24 pass through a clearance region between the detector rings 12a and 12b and are irradiated to a treatment range of the patient 6, without interfering with the PET gantries (60a, 60b). The radiation therapy device 24 is controlled by a medical device control system 26. The clearance between the detector rings 12a and 12b is determined so that the particle beams 22 will not interfere with the PET gantries (60a, 60b). The thus obtained PET image is fed back to the medical device control system 26 and used for confirmation of the therapeutic effects or altering treatment plans.

Figure 26:
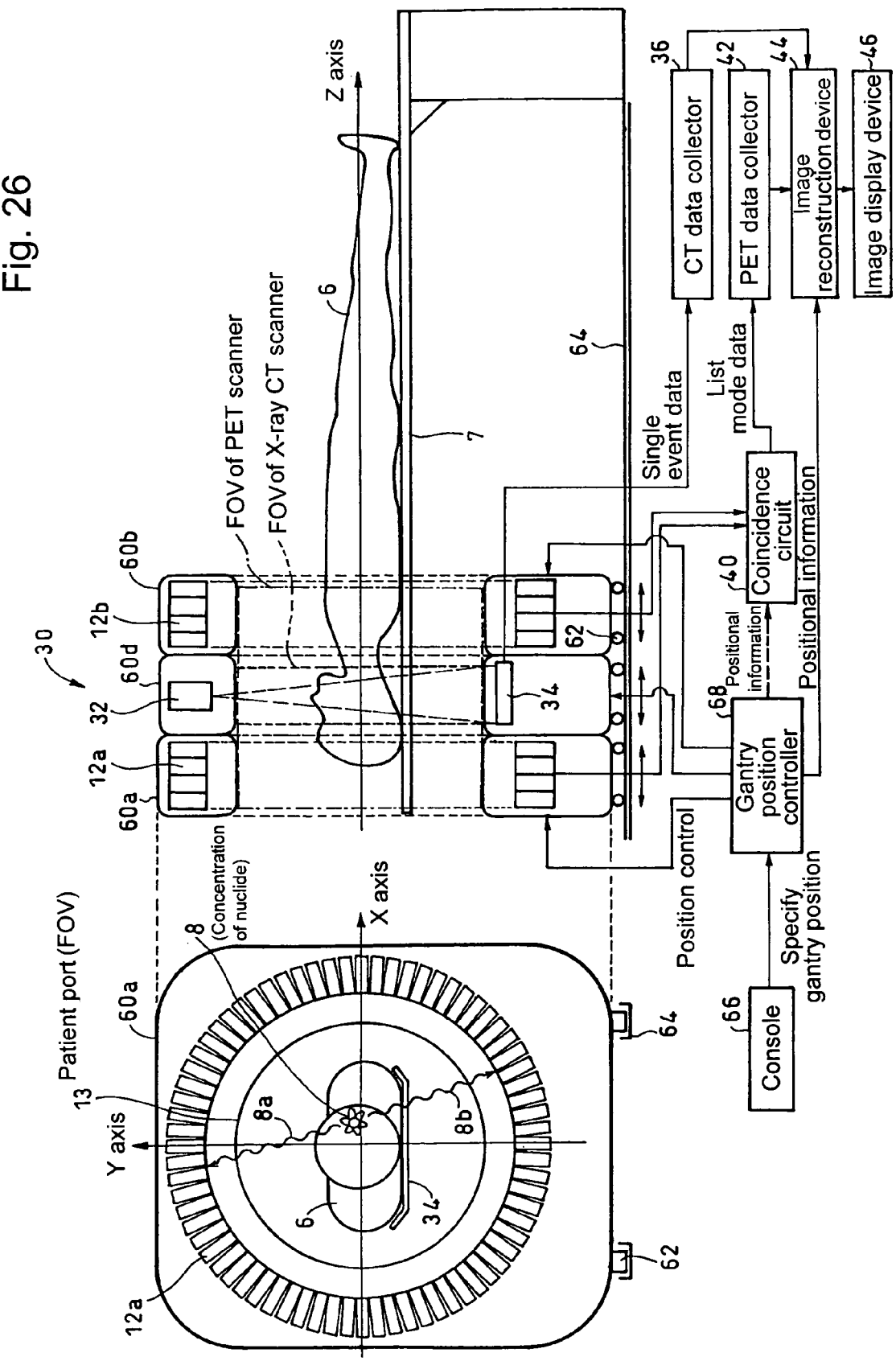
FIG. 26 is a drawing illustrating a fourth example of the present invention.

FIG. 26 illustrates a constitution of the fourth example of a PET scanner in which X-ray CT scanner 30 is installed at a clearance region between the detector rings 12a and 12b, in a PET scanner in which two identical detector rings 12a, 12b formed in a ring shape are arranged in tandem as independent gantries (60a, 60b) and a clearance between the detector rings 12a and 12b is made variable, thus making it possible to image the same site during the same session with the X-ray CT.

The X-ray CT scanner 30 is constituted with an X-ray tube 32 and an X-ray detector 34 which mutually rotates. The detector rings 12a and 12b of the PET scanner and the X-ray CT scanner 30 may be fixed at their positions and constituted in an integrated manner. However, FIG. 26 illustrates a constitution in which they are respectively provided with independent gantries (60a, 60b, 60d) and arranged in tandem on a common or an independent rail 64 and constituted so as to move in the back and forth direction.

The detector rings 12a and 12b of the PET scanner and the X-ray CT scanner 30 are controlled at their respective positions by a common gantry position controller 68.

The CT data collector 36 which stores the data of the X-ray CT scanner 30 in a recording medium may be common with the PET data collector 42. An image reconstruction device for the X-ray CT scanner 30 may be independent of that for the PET scanner. In the present constitution, a common image reconstruction device 44 is used to image the data of the X-ray CT scanner 30 and that of the PET scanner which are then superimposed, and the thus superimposed image is displayed on an image display device 46.

Figure 27:
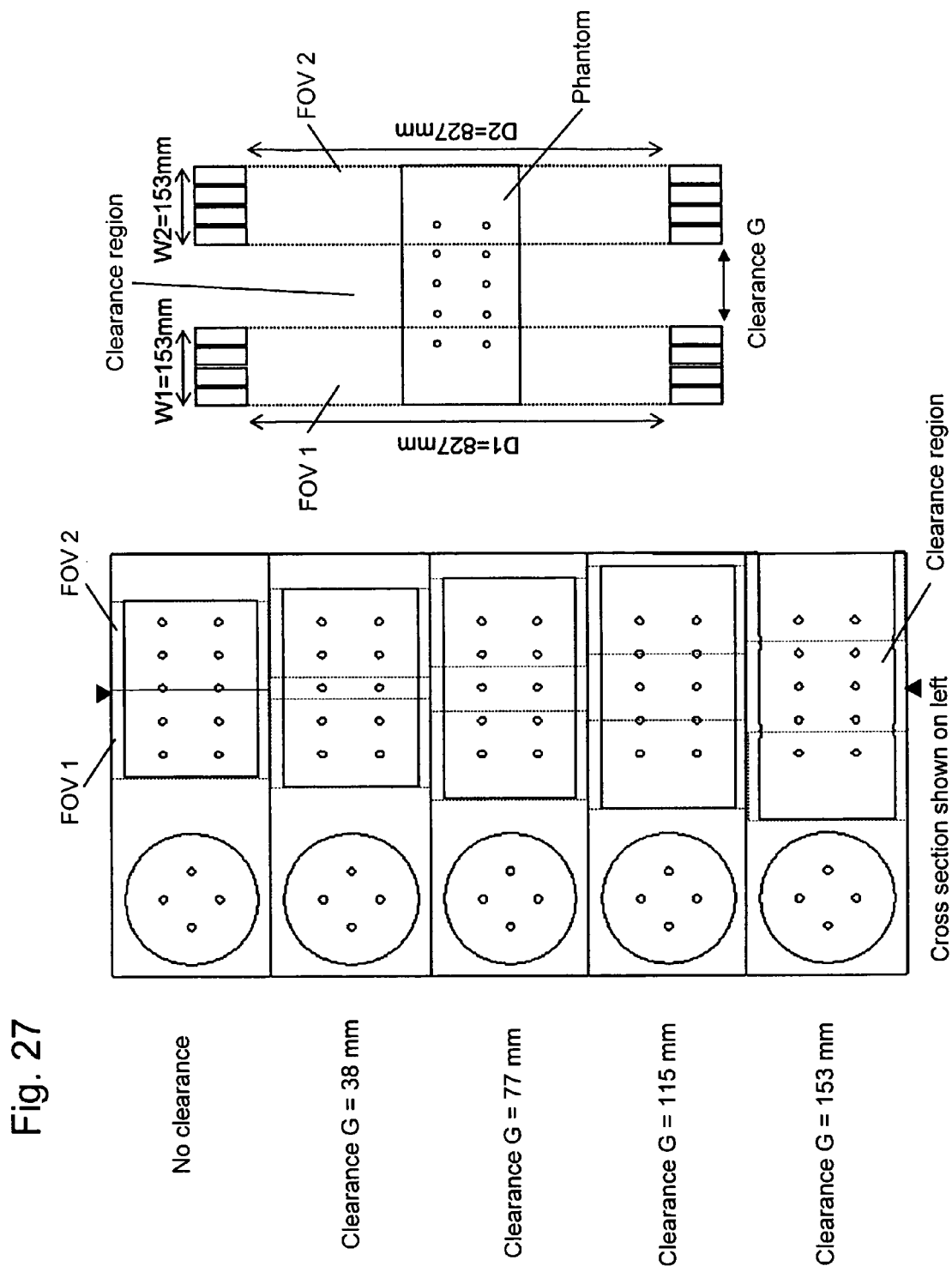
FIG. 27 is a drawing illustrating one example of computer simulation results.

FIG. 27 illustrates an example where a PET scanner in which two identical detector rings formed in a ring shape are arranged in tandem to make variable a clearance between the detector rings is subjected to computer simulation, thereby performing image reconstruction. The diameters of the detector rings are D1=D2=827 mm, and the widths of the sensitivity areas in the body axis direction are W1=W2=153 mm. Each of the detector rings is constituted in such a manner that Bismuth Germanium Oxide (BGO) measuring 4.05 mm (cross sectional direction)×4.39 mm (body axis direction)×30 mm (depth direction) is used as a detecting element and these detecting elements are arranged so as to give 8 lines by 8 rows, with a clearance of 0.4 mm kept from each other, thereby giving one detector block, and 72 of these detector blocks are arranged in an arc around the circumference of the gantry in four rows in the body axis direction. A clearance G between the detector rings is allowed to change in five different ways, that is, 0 mm (no clearance), 38 mm, 77 mm, 115 mm and 153 mm. A numerical phantom was simulated in a case where a total of 20 spherical bodies with a diameter of 9.6 mm were arranged three dimensionally inside a cylinder measuring 23 cm in diameter and 46 cm in length in the body axis direction and a nuclide was sealed so as to give a relative strength of 1 in the entire cylinder and a relative strength of 2 in 20 spherical bodies. Thereby, it has been confirmed that even if the clearance G between the detector rings is expanded up to 153 mm, a reconstruction image is obtained, which is equal in quality to that obtained when no clearance is provided.

Figure 28:
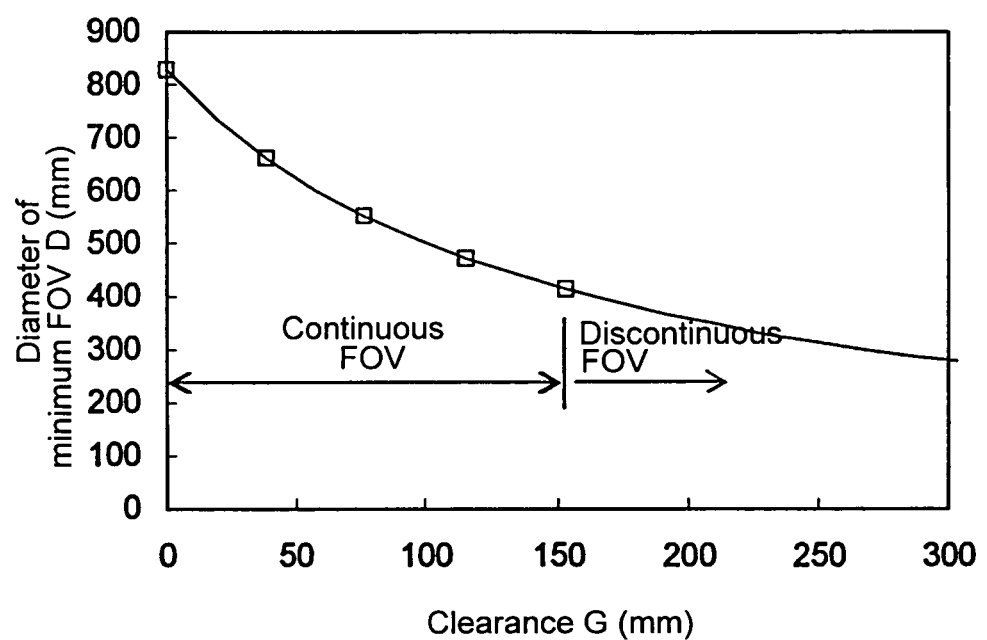
FIG. 28 is a drawing illustrating one example of calculation of the allowable range in which the detector rings may be arranged.

FIG. 28 shows the results obtained by allowing the clearance G between the detector rings to change with respect to parameters of the above PET scanner, thereby studying the diameter D of a minimum FOV and the continuity of FOVs in the body axis direction. The diameter D of a minimum FOV is D=827 mm which is the same as the diameter of the detector ring where no clearance is provided. However, when the clearance G is set to be 153 mm, the diameter is decreased to D=414 mm. Further, the clearance G between the detector rings which is equal to 153 mm is a limit by which the FOV can be secured continuously in the body axis direction. Where the clearance is made greater than the above, it is clear that the FOV is no longer secured continuously in the body axis direction.

Figure 29:
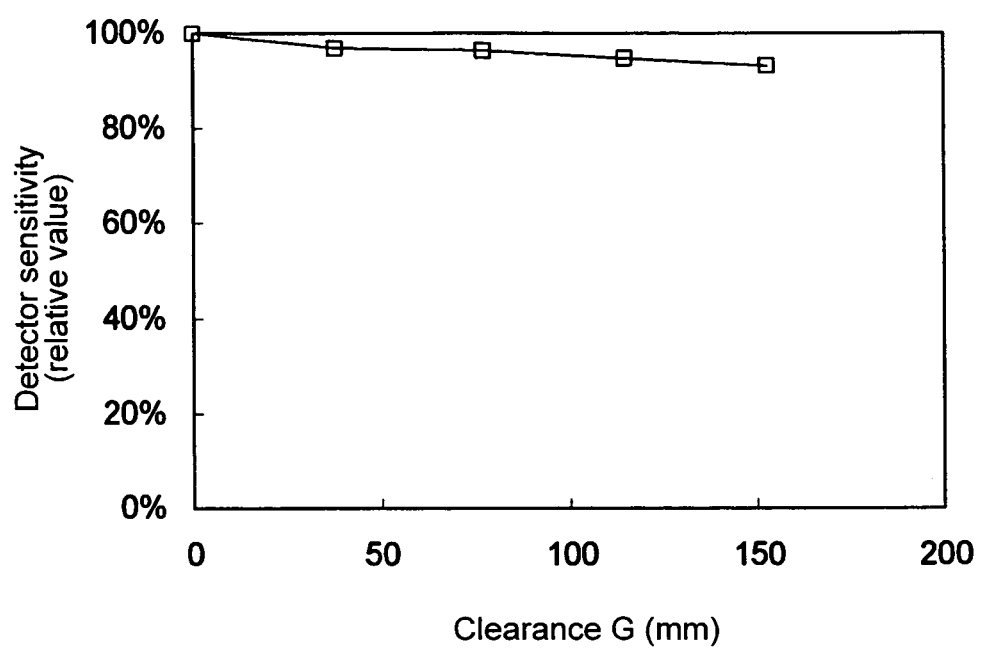
FIG. 29 is a drawing illustrating simulation results of the detector sensitivity.

FIG. 29 is a drawing in which the sensitivities of detectors as a whole obtained by allowing the clearance G between the detector rings to change are plotted relatively, with a case of no clearance given as 100%. Although a small decrease in sensitivity due to the change in solid angle is found, it is clear that an expanded clearance between the detector rings only slightly affects the detector sensitivity.

The present invention is mounted on a test machine of a PET scanner for the head to study the effect thereof. Since a main object is to study the influence on the quality of an image, the determination data was damaged artificially in place of mechanical movement of the detectors.

Figure 30:
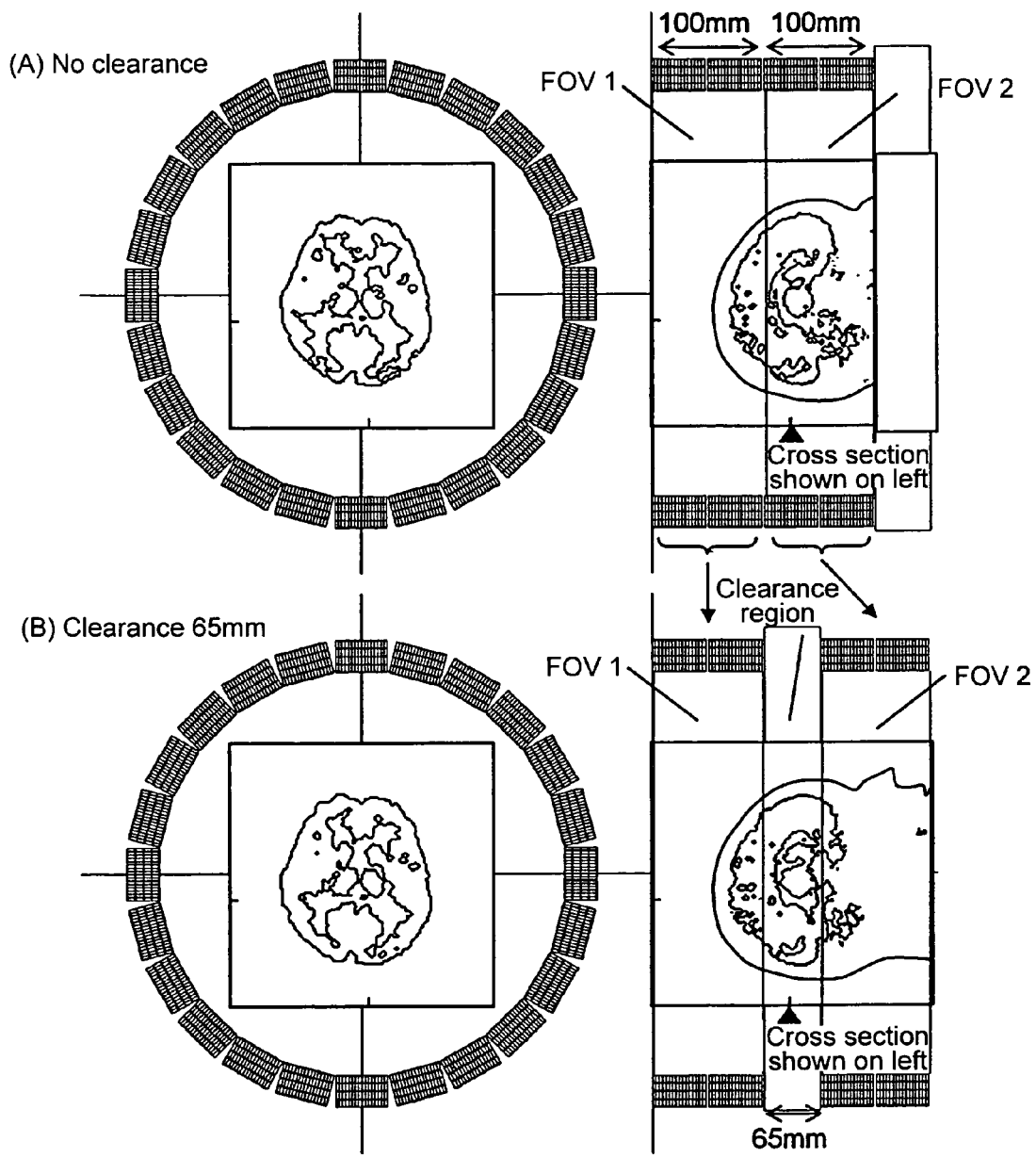
FIG. 30 is a drawing illustrating experimental results.

FIG. 30 illustrates the results in which where two identical detector rings having a FOV of 100 mm in the body axis direction are arranged, with no clearance kept (A) and with the clearance of 65 mm kept (B), experimental data with healthy people is used to reconstruct an image according to a three-dimensional successive approximation. The drawing on the left side of FIG. 30 (B) illustrates a tomographic image of the clearance region, the quality of which is clearly equal to the image given in FIG. 30 (A) where no clearance is provided.

In the above embodiments, a complete open space between individual detector rings is provided. However, detectors are arranged at unnecessary open spaces, thus making it possible to improve the detector sensitivity and also improve the quality of a PET image.

Figure 31:
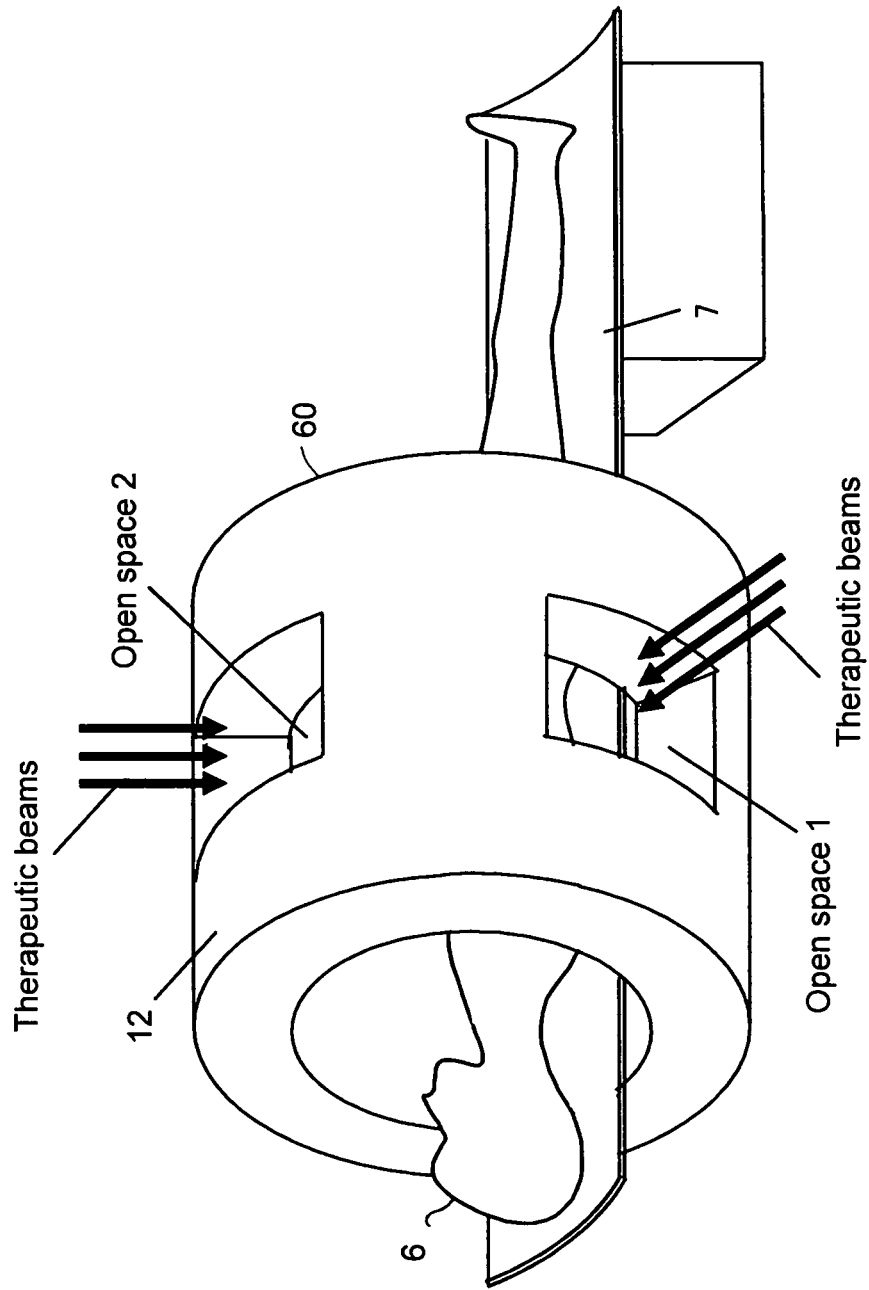
FIG. 31 is a drawing illustrating a modified example.

Specifically, where irradiation beams of radiotherapy can be controlled for the irradiation direction, as illustrated in FIG. 31, detectors can be arranged at spaces excluding routes of therapeutic beams.

Figure 32:
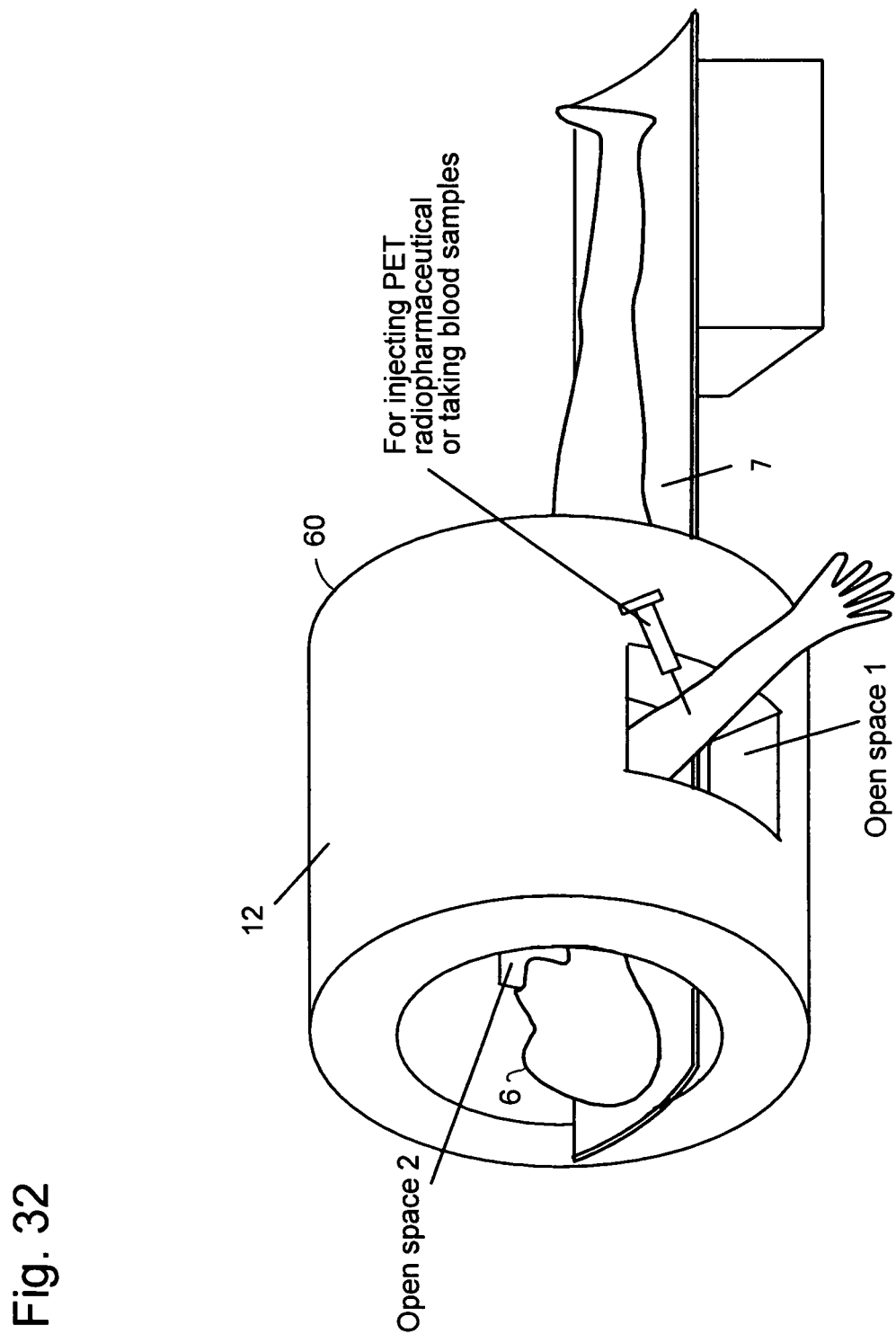
FIG. 32 is a drawing illustrating another modified example.

Further, as illustrated in FIG. 32, on ordinary PET scanning, in order to gain access to the arms of a patient 6 from outside the gantry 60, an open space may be provided only at two sites near the arms. Thereby, it is possible to easily inject a PET radiopharmaceutical before check-ups or collect blood samples during PET scanning.

Figure 33:
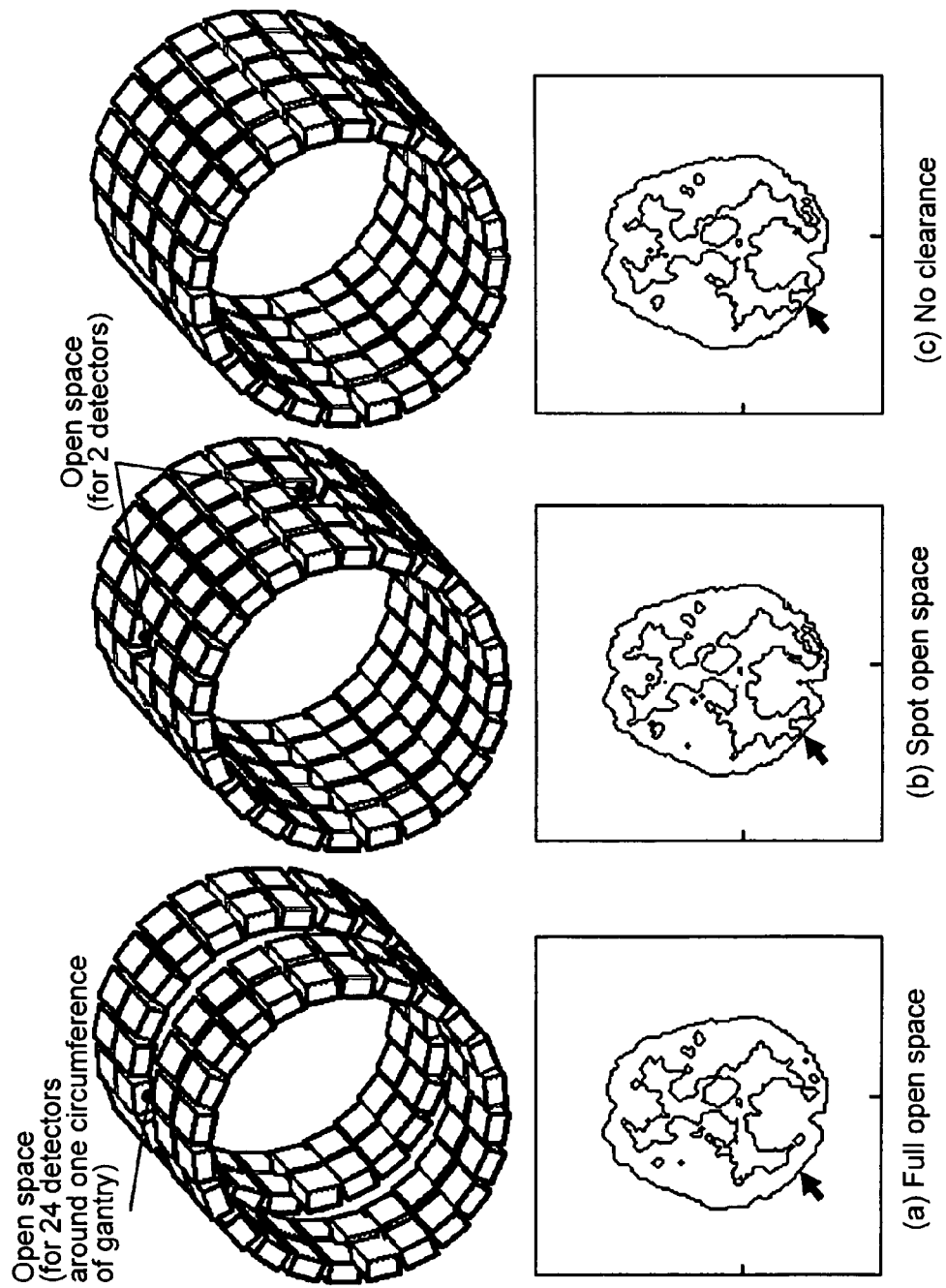
FIG. 33 is a drawing illustrating experimental results of the modified example.

FIG. 33 illustrates the results of experimental studies in which detectors are arranged at unnecessary open spaces to obtain improvement effects of the quality of an image. As illustrated in (A), where a full open space at which a central detector ring is removed is provided, there is a case where some of the detailed structures of the brain may not be correctly imaged as indicated by the arrow in the drawing, as compared with a case where no clearance is provided as illustrated in (C). However, as illustrated in (B), where spot open spaces are provided at which detectors are arranged at sites excluding two open spaces, results are obtained which are similar to those where no clearance is provided as illustrated in (C).

INDUSTRIAL APPLICABILITY

The present invention is able to provide an open-type PET scanner capable of easily gaining access to a patient under PET scanning from outside a gantry and also providing irradiation of particle beams for cancer treatment as well as X-ray CT scanning.

What is claimed is:

1. A Positron Emission Tomography (PET) scanner comprising:
   a gantry; and
   a plurality of sets of detector rings, each set including a plurality of detector rings, with an open space between the sets of detector rings kept in the body axis direction, wherein
   each detector ring comprises detectors that are arranged densely or spatially in a ring shape or in a polygonal shape,
   coincidences are measured for some of or all of detector pairs connecting the sets of detector rings apart from the open space to perform three-dimensional image reconstruction, thereby imaging the open space between the sets of detector rings as a tomographic image, and
   the gantry is completely or partially separated horizontally at the open space, allowing access to a patient from outside the gantry.

2. The PET scanner according to claim 1, wherein the coincidences are measured not only for some of or all of detector pairs connecting the sets of detector rings apart from the open space but also for some of or all of detector pairs within the same detector rings to perform the three-dimensional image reconstruction, thus making it possible to image as a tomographic image a continuous region which combines a field-of-view within each of the detector rings with the open space.

3. The PET scanner according to claim 1, wherein, among open spaces secured between sets of detector rings, detectors are arranged at open spaces among sets of detector rings, thus making it possible to improve the detector sensitivity and also improve the quality of a PET image.

4. The PET scanner according to claim 1, wherein
   each set of detector rings is structured so as to translate in the back and forth direction, and a clearance between the sets of detector rings in the body axis direction is made variable.

5. The PET scanner according to claim 1, wherein the PET scanner is configured to monitor treatment to a site by a therapeutic beam, where the therapeutic beam is configured to pass through the open space between the sets of detector ring.

6. The PET scanner according to claim 1, wherein when an X-ray Computed Tomography (CT) scanner is inserted at least partially into a clearance region between sets of detector rings to image a site, the PET scanner simultaneously images the site.

7. The PET scanner according to claim 1, wherein
   a sensitivity width defines a width of a field of view of the PET scanner in the open space between a first set of detector rings and a second set of detector rings,
   a diameter and a width of the first set of detector rings, a diameter and a width of the second set of detector rings, and a width of the open space are configured such that the sensitivity width is greater than the width of the open space in a body axis direction,
   the sensitivity width overlaps an edge of the first set of detector rings adjacent to the open space and an edge of the second set of detector rings adjacent to the open space in the body axis direction, and
   a diameter of the field of view of the PET scanner in the open space is greater than an examination target region to be imaged.

8. An image reconstruction method for a Positron Emission Tomography (PET) scanner, wherein on calculating image reconstruction of the PET scanner described in claim 1, a system matrix to be calculated or referred is changed in accordance with the arrangement of detectors.

* * * * *